United States Patent [19]

Jaetsch et al.

[11] Patent Number: 5,679,675
[45] Date of Patent: *Oct. 21, 1997

[54] 8-AMINO-10-(AZABICYCLOALKYL)-PYRIDO [1,2,3-D,E][1,3,4]BENZOXADIAZINE DERIVATIVES

[75] Inventors: Thomas Jaetsch, Köln; Burkhard Mielke; Uwe Petersen, both of Leverkusen; Thomas Schenke, Bergisch Gladbach; Klaus-Dieter Bremm, Recklinghausen; Rainer Endermann, Wuppertal; Karl-Georg Metzger, Wuppertal; Martin Scheer, Wuppertal; Michael Stegemann; Heinz-Georg Wetzstein, both of Leverkusen, all of Germany

[73] Assignee: Bayer Aktiengesellschaft, Leverkusen, Germany

[*] Notice: The term of this patent shall not extend beyond the expiration date of Pat. No. 5,508,278.

[21] Appl. No.: 434,806

[22] Filed: May 4, 1995

[30] Foreign Application Priority Data

May 11, 1994 [DE] Germany .............. 44 16 622.2

[51] Int. Cl.⁶ .............. A61K 31/535; C07D 498/06; C07D 519/00
[52] U.S. Cl. .............. 514/229.2; 544/66
[58] Field of Search .............. 544/66; 514/229.2

[56] References Cited

U.S. PATENT DOCUMENTS

| 4,988,709 | 1/1991 | Ogata | 514/314 |
| 4,990,517 | 2/1991 | Petersen | 514/300 |
| 5,245,037 | 9/1993 | Kuramoto | 546/156 |
| 5,508,278 | 4/1996 | Jaetsch et al. | 514/229.2 |

FOREIGN PATENT DOCUMENTS

| 0259804 | 3/1988 | European Pat. Off. |
| 0343524 | 11/1989 | European Pat. Off. |
| 4329600 | 3/1995 | Germany |

OTHER PUBLICATIONS

Jaetsch et al, Chem. Abstract 123:9466 (1995) For De 4329600 (Mar. 9, 1995).

T. Culbertson et al., J. Med. Chem., vol. 33, pp. 2270–2275 (1990).

M. Ogata et al., Eur. J. Med. Chem., vol. 26, pp. 889–906 (1991).

J.M. Domogala, J. Med. Chem., vol. 31, No. 3, pp. 503–506 (1988).

Miyamoto et al., J. Med. Chem. vol. 33, pp. 1645–1656 (1990).

*Primary Examiner*—Philip I. Datlow
*Attorney, Agent, or Firm*—Sprung Kramer Schaefer & Briscoe

[57] ABSTRACT

The present invention relates to new 8-amino-10-(azabicycloalkyl)-pyrido[1,2,3-d,e][1,3,4]benzoxadiazine derivatives of the general formula (I)

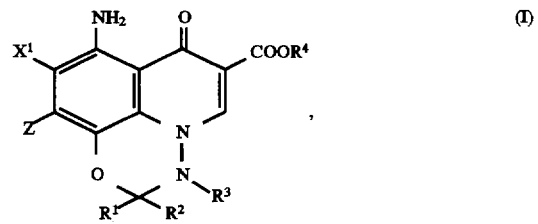

in which the radicals $R^1$ to $R^4$, Z and $X^1$ have the meaning given in the description, processes for their preparation and their use in antibacterial compositions.

6 Claims, No Drawings

8-AMINO-10-(AZABICYCLOALKYL)-PYRIDO [1,2,3-D,E][1,3,4]BENZOXADIAZINE DERIVATIVES

The present invention relates to new 8-amino-10-(azabicycloalkyl)-pyrido[1,2,3-d,e][1,3,4]benzoxadiazine derivatives, processes for their preparation, and antibacterial compositions containing these compounds.

It has already been disclosed that pyridobenzoxadiazinecarboxylic acids of this type are antibacterially active. Examples of these are found in EP-0 259 804, EP-0 343 524 and in the European Journal of Medicinal Chemistry 26, 889 (1991).

The present invention relates to:
1. New 8-amino-10-(azabicycloalkyl)-pyrido[1,2,3-d,e][1,3,4]benzoxadiazine derivatives of the general formula (I)

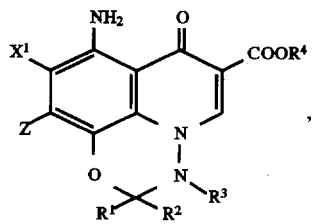

in which
$R^1$ represents hydrogen or $C_1$-$C_4$-alkyl which is optionally substituted by hydroxyl or halogen,
$R^2$ independently of $R^1$ represents hydrogen or methyl,
$R^3$ represents hydrogen or $C_1$-$C_4$-alkyl,
$R^4$ represents hydrogen, alkyl having 1 to 4 carbon atoms, which is optionally substituted by hydroxyl, methoxy, amino, methylamino or dimethylamino, or (5-methyl-2-oxo-1,3-dioxol-4-yl)-methyl,
$X^1$ represents hydrogen or halogen,
Z represents radicals with the structures

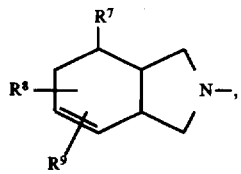

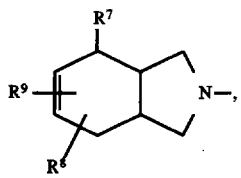

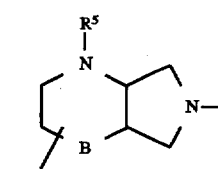

in which
$R^7$ represents hydrogen, hydroxyl, —$NR^{10}R^{11}$, hydroxymethyl, —$CH_2$—$NR^{10}R^{11}$, carboxyl, methoxycarbonyl or ethoxycarbonyl, where
$R^{10}$ represents hydrogen, $C_1$-$C_3$-alkyl which is optionally substituted by hydroxyl, alkoxycarbonyl having 1 to 4 C atoms in the alkoxy moiety or $C_1$-$C_3$-acyl, $R^{11}$ represents hydrogen or methyl,
$R^8$ represents hydrogen, straight-chain or branched $C_1$-$C_3$-alkyl or cyclopropyl,
$R^9$ represents hydrogen or methyl,
$R^6$ represents hydrogen or methyl,
$R^5$ represents hydrogen, methyl or radicals with the structures —CH=CH—$CO_2R^{5'}$, —$CH_2$—$CH_2$—$CO_2R^{5'}$, —$CH_2$—CO—$CH_3$, —$CH_2$—$CH_2$—CN,
$R^{5'}$ represents methyl or ethyl,
B represents —$CH_2$—, O or a direct bond.

The compounds of the formula (I) can be present in the form of racemates or as enantiomerically pure compounds, and in the form of their pharmaceutically utilizable hydrates and acid addition salts, and in the form of their alkali, alkaline earth, silver and guanidinium salts.

2. Process for the preparation of the New 8-amino-10-(azabicycloalkyl-pyrido[1,2,3-d,e][1,3,4]benzoxadiazine derivatives of the general formula (I)

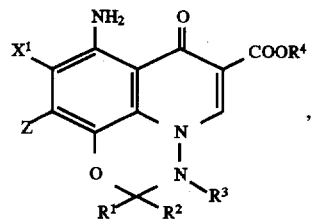

in which
$R^1$ represents hydrogen or $C_1$-$C_4$-alkyl which is optionally substituted by hydroxyl or halogen,
$R^2$ independently of $R^1$ represents hydrogen or methyl,
$R^3$ represents hydrogen or $C_1$-$C_4$-alkyl,
$R^4$ represents hydrogen, alkyl having 1 to 4 carbon atoms, which is optionally substituted by hydroxyl, methoxy, amino, methylamino or dimethylamino, or (5-methyl-2-oxo-1,3-dioxol-4-yl)-methyl,
$X^1$ represents hydrogen or halogen,
Z represents radicals with the structures

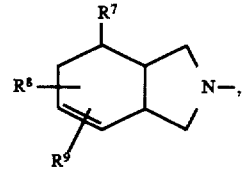

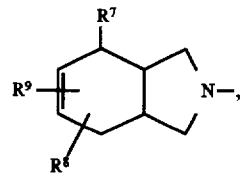

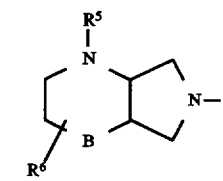

in which
$R^7$ represents hydrogen, hydroxyl, —$NR^{10}R^{11}$, hydroxymethyl, —$CH_2$—$NR^{10}R^{11}$, carboxyl, methoxycarbonyl or ethoxycarbonyl, where $R^{10}$ represents hydrogen, $C_1$–$C_3$-alkyl which is optionally substituted by hydroxyl, alkoxycarbonyl having 1 to 4 C atoms in the alkoxy moiety or $C_1$–$C_3$-acyl, $R^{11}$ represents hydrogen or methyl, $R^8$ represents hydrogen, straight-chain or branched $C_1$–$C_3$-alkyl or cyclopropyl, $R^9$ represents hydrogen or methyl, $R^6$ represents hydrogen or methyl, $R^5$ represents hydrogen, methyl or radicals with the structures —CH=CH—$CO_2R^{5'}$, —$CH_2$—$CH_2$—$CO_2R^{5'}$, —$CH_2$—CO—$CH_3$, —$CH_2$—$CH_2$—CN, $R^{5'}$ represents methyl or ethyl, B represents —$CH_2$—, O or a direct bond, characterized in that compounds of the formula (II)

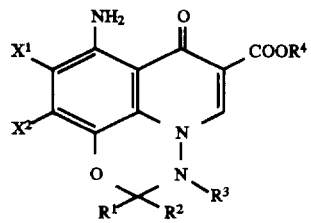

(II)

in which $R^1$, $R^2$, $R^3$, $R^4$ and $X^1$ have the meaning given above and $X^2$ represents halogen, in particular fluorine or chlorine, are reacted with compounds of the formula (III)

Z—H   (III)

in which

Z has the meaning given above, if appropriate in the presence of acid-binding agents.

3. Compounds of the formula (II)

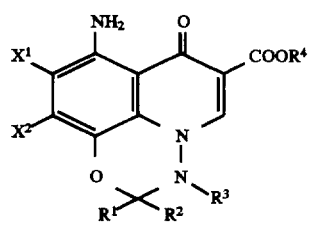

(II)

in which $R^1$, $R^2$, $R^3$, $R^4$ and $X^1$ have the meaning given under section 1 and $X^2$ represents halogen.

4. Process for the preparation of the compounds of the formula (II) characterized in that compounds of the formula (IV)

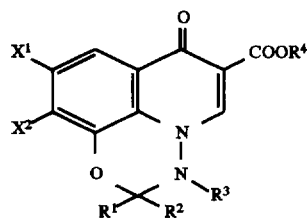

(IV)

in which $R^1$, $R^2$, $R^3$, $R^4$, $X^1$ and $X^2$ have the meaning given under section 3, are reacted with nitrating reagents and the nitro compounds obtained are then reduced.

In comparison with known representatives of this structural type, the compounds according to the invention have a higher antibacterial action, in particular in the Gram-positive range. They are therefore suitable as active compounds for human and veterinary medicine.

Preferred compounds of the formula (I) are those in which $R^1$ represents hydrogen or $C_1$–$C_3$-alkyl which is optionally substituted by hydroxyl, $R^2$ independently of $R^1$ represents hydrogen or methyl, $R^3$ represents hydrogen, methyl or ethyl, $R^4$ represents hydrogen, alkyl having 1 to 4 carbon atoms, which is optionally substituted by hydroxyl, methoxy, amino, methylamino or dimethylamino, or (5-methyl-2-oxo-1,3-dioxol-4-yl)-methyl, $X^1$ represents hydrogen, fluorine or chlorine, Z represents radicals with the structures

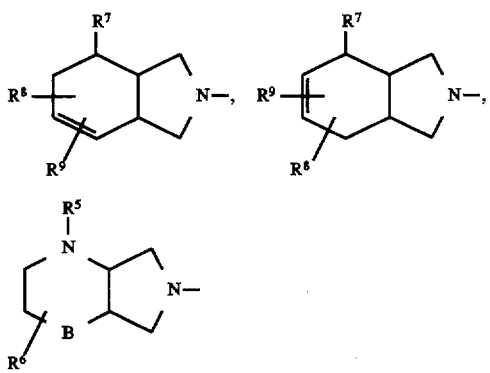

in which $R^7$ represents hydrogen, hydroxyl, —$NR^{10}R^{11}$, hydroxymethyl or —$CH_2$—$NR^{10}R^{11}$, where $R^{10}$ represents hydrogen, $C_1$–$C_2$-alkyl which is optionally substituted by hydroxyl, alkoxycarbonyl having 1 to 4 C atoms in the alkoxy moiety or $C_1$–$C_3$-acyl, $R^{11}$ represents hydrogen or methyl, $R^8$ represents hydrogen, straight-chain or branched $C_1$–$C_3$-alkyl or cyclopropyl, $R^9$ represents hydrogen or methyl, $R^5$ represents hydrogen or methyl, $R^6$ represents hydrogen, B represents —$CH_2$—, O or a direct bond and their pharmaceutically utilizable hydrates and acid addition salts, and their alkali metal, alkaline earth metal, silver and guanidinium salts.

Particularly preferred compounds of the formula (I) are those in which $R^1$ represents hydrogen or methyl, $R^2$ represents hydrogen, $R^3$ represents methyl or ethyl, $R^4$ represents hydrogen, methyl or ethyl, $X^1$ represents fluorine, Z represents radicals with the structures

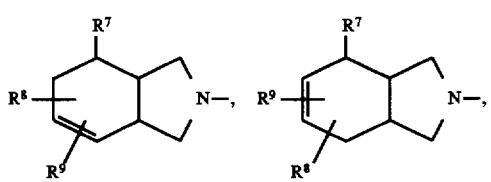

-continued

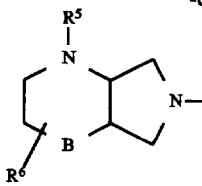

in which

R⁷ represents hydrogen, hydroxyl, —NR¹⁰R¹¹, hydroxymethyl or —CH₂—NR¹⁰R¹¹, where
  R¹⁰ represents hydrogen, methyl, alkoxycarbonyl having 1 to 4 C atoms in the alkoxy moiety or C₁–C₃-acyl, R¹¹ represents hydrogen or methyl, R⁸ represents hydrogen, straight-chain or branched C₁–C₃-alkyl or cyclopropyl, R⁶ represents hydrogen, R⁹ represents hydrogen or methyl, R⁵ represents hydrogen or methyl, B represents —CH₂—, O or a direct bond and their pharmaceutically utilizable hydrates and acid addition salts, and their alkali metal, alkaline earth metal, silver and guanidinium salts.

The following compounds of the formula (I) may be mentioned in detail:

| R¹ | R³ | R⁴ | Z | X |
|----|----|----|---|---|

(Formula I shown at top of table)

| R¹ | R³ | R⁴ | Z | X |
|----|----|----|---|---|
| H | Me | H | (N-methyl piperidine-pyrrolidine bicyclic) | F |
| H | Me | H | (N-methyl morpholine-pyrrolidine bicyclic) | F |
| H | Me | H | (N-methyl pyrrolidine-pyrrolidine bicyclic) | F |
| H | Me | Et | (NH piperidine-pyrrolidine bicyclic) | F |
| H | Et | H | (NH piperidine-pyrrolidine bicyclic) | F |
| Me | Me | H | (NH piperidine-pyrrolidine bicyclic) | F |

-continued
| R¹ | R³ | R⁴ | Z | X |
|---|---|---|---|---|
| Me | Me | H | 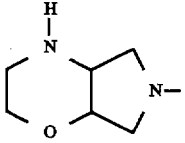 | F |
| CH₂OH | Me | H | 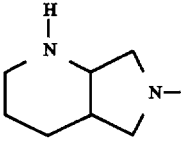 | F |
| H | H | H | 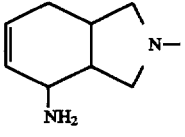 | F |
| H | H | Ethyl | 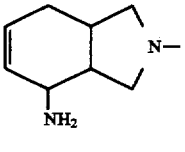 | F |
| H | H | H | 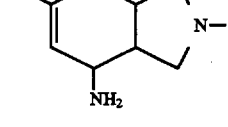 | F |
| H | H | H | 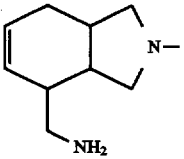 | F |
| CH₃ | H | Ethyl | 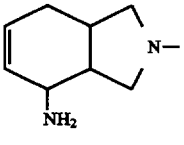 | F |
| H | H | —CH₂—CH₂—NH₂ | 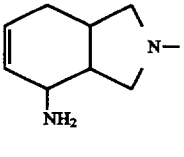 | F |
| H | H | —CH₂—CH₂—OCH₃ | 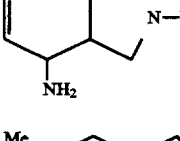 | F |
| CH₃ | H | H | 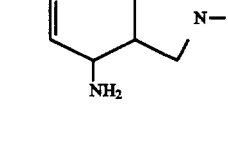 | F |

-continued
| R¹ | R³ | R⁴ | Z | X |
|---|---|---|---|---|
| CH₃ | CH₃ | H | 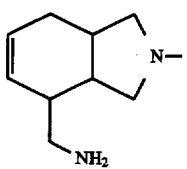 | F |
| H | CH₃ | Ethyl | 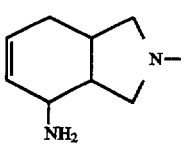 | F |
| H | CH₃ | —CH₂—CH₂—NH₂ | 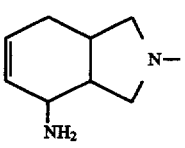 | F |
| H | CH₃ | —CH₂—CH₂—OCH₃ | 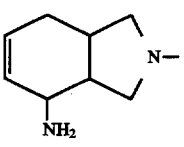 | F |
| H | H | Ethyl | 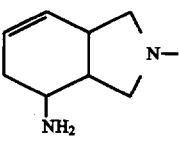 | F |
| CH₃ | H | H | 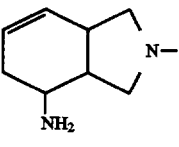 | F |
| CH₃ | CH₃ | H | 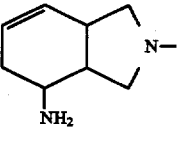 | F |
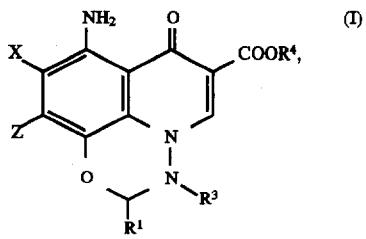
(I)
| H | Me | H | 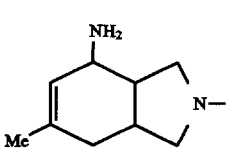 | F |

-continued
| R¹ | R³ | R⁴ | Z | X |
|---|---|---|---|---|
| H | Me | H | 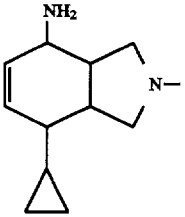 | F |
| H | Me | H | 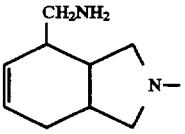 | F |
| H | Et | H | 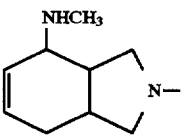 | F |
| Me | Me | H | 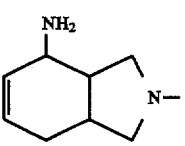 | F |
| CH₂OH | Me | H | 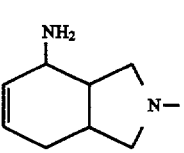 | F |
| H | Me | H | 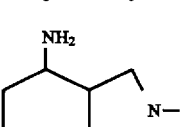 | F |
| H | Me | H | 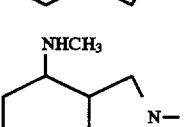 | F |
| H | Me | H | 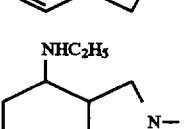 | F |
| H | Me | H | 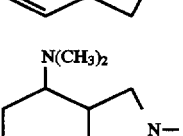 | F |
| H | Me | H | 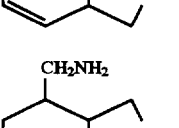 | F |

-continued
| R¹ | R³ | R⁴ | Z | X |
|---|---|---|---|---|
| H | Me | H | 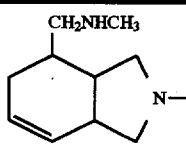 CH₂NHCH₃ | F |
| H | Me | H | 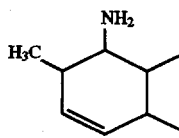 NH₂, H₃C | F |
| H | Me | H | 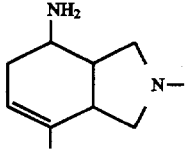 NH₂, CH₃ | F |
| H | Me | H | 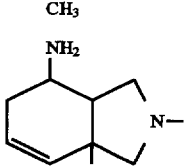 NH₂, CH₃ | F |
| H | Me | H | 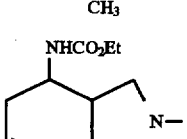 NHCO₂Et | F |
| H | Me | H | 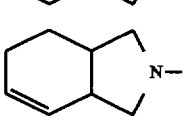 | F |
| H | Me | H | 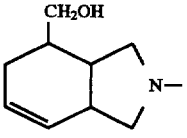 CH₂OH | F |
| H | Me | H | 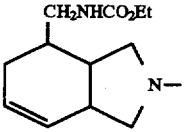 CH₂NHCO₂Et | F |
| Me | Me | H | 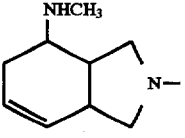 NHCH₃ | F |
| Me | Me | H | 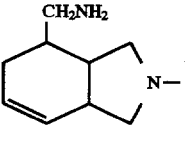 CH₂NH₂ | F |
| CH₂OH | Me | H | 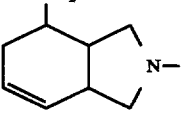 NH₂ | F |

-continued

| R¹ | R³ | R⁴ | Z | X |
|---|---|---|---|---|
| CH₂OH | Me | H | (NHCH₃-substituted bicyclic amine) | F |
| CH₂OH | Me | H | (CH₂NH₂-substituted bicyclic amine) | F |
| H | Et | H | (NH₂-substituted bicyclic amine) | F |
| H | Et | H | (NHCH₃-substituted bicyclic amine) | F |
| H | Me | Et | (NH₂-substituted bicyclic amine) | F |
| H | Me | Et | (NHCH₃-substituted bicyclic amine) | F |

If, for example, 8-amino-9,10-difluoro-3-methyl-7-oxo-2,3-dihydro-7H-pyrido[1,2,3-d,e][1,3,4]benzoxadiazine-6-carboxylic acid and 2,8-diazabicyclo[4.3.0]nonane are used for the preparation of compounds of the formula (I), the course of the reaction can be represented by the following equation:

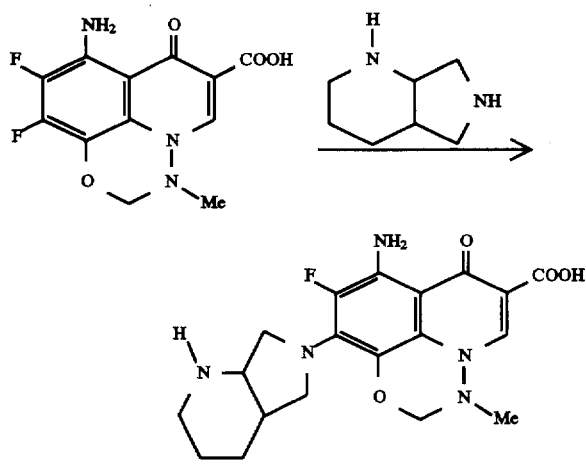

The compounds of the formula (II) used as starting compounds are new. They can be prepared by reacting compounds of the formula (IV)

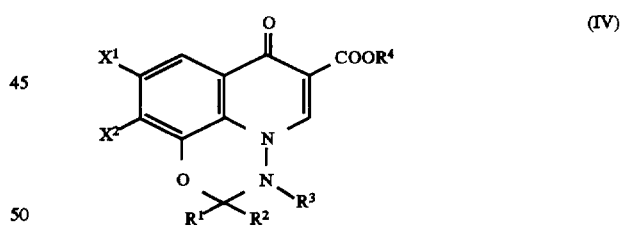

(IV)

in which R¹, R², R³, R⁴, X¹ and X² have the meaning given above, with nitrating reagents such as nitric acid and nitrates in a solvent such as, for example, water, sulphuric acid, acetic acid, acetic anhydride or mixtures thereof at −50° to 200° C., preferably at −20° to 100° C., and then reducing the nitro compounds obtained.

Metal hydrides, transition metals and transition metal salts can be employed for the reduction of the nitro group; hydrogen is preferably used in the presence of catalysis such as, for example, palladium-carbon, Raney nickel and platinum. Solvents which can be used are, for example, water, hydrochloric acid, alcohols, acetic acid or alternatively mixtures thereof.

Compounds of the formula (II) can also be prepared according to the following reaction scheme, in which R¹, R², R³, R⁴, X¹ and X² have the meaning given above:

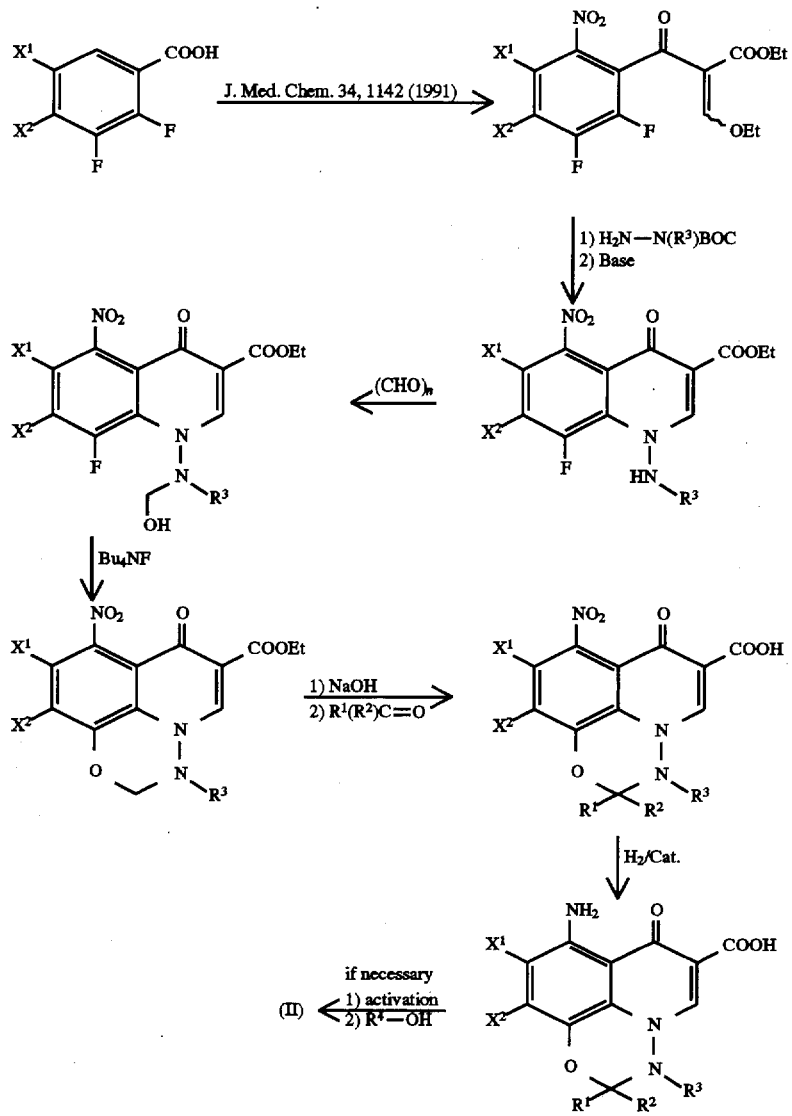

They can optionally be employed as racemates, enantiomers or pure diastereomers.

Examples which may be mentioned are:
8-amino-9,10-difluoro-3-methyl-7-oxo-2,3-dihydro-7H-pyrido[1,2,3-d,e][1,3,4]benzoxadiazine-6-carboxylic acid
8-amino-9,10-difluoro-2,3-dimethyl-7-oxo-2,3-dihydro-7H-pyrido[1,2,3-d,e][1,3,4]benzoxadiazine-6-carboxylic acid
8-amino-9,10-difluoro-2-(hydroxymethyl)-3-methyl-7-oxo-2,3-dihydro-7H-pyrido[1,2,3-d,e]-[1,3,4]benzoxadiazine-6-carboxylic acid
8-amino-9,10-difluoro-3-ethyl-7-oxo-2,3-dihydro-7H-pyrido[1,2,3-d,e][1,3,4]benzoxadiazine-6-carboxylic acid ethyl
8-amino-9,10-difluoro-3-methyl-7-oxo-2,3-dihydro-7H-pyrido[1,2,3-d,e][1,3,4]benzoxadiazine-6-carboxylate The amines of the formula (III) used as starting compounds are known. Chiral amines can be employed both as racemates, and as enantiomerically or diastereomerically pure compounds.

Examples which may be mentioned are:
2,7-diazabicyclo[3.3.0]octane
2-methyl-2,7-diazabicyclo[3.3.0]octane
2,8-diazabicyclo[4.3.0]nonane
2-methyl-2,8-diazabicyclo[4.3.0]nonane
2-oxa-5,8-diazabicyclo[4.3.0]nonane
5-methyl-2-oxa-5,8-diazabicyclo[4.3.0]nonane
2-amino-8-azabicyclo[4.3.0]non-3-ene
2-methylamino-8-azabicyclo[4.3.0]non-3-ene
4-methyl-2-methylamino-8-azabicyclo[4.3.0]non-3-ene
5-methyl-2-methylamino-8-azabicyclo[4.3.0]non-3-ene
2-dimethylamino-8-azabicyclo[4.3.0]non-3-ene
2-ethylamino-8-azabicyclo[4.3.0]non-3-ene
2-methylaminomethyl-8-azabicyclo[4.3.0]non-3-ene
2-hydroxy-8-azabicyclo[4.3.0]non-3-ene
5-isopropyl-2-methylamino-8-azabicyclo[4.3.0]non-3-ene
2-amino-5-isopropyl-8-azabicyclo[4.3.0]non-3-ene
2-amino-5-methyl-8-azabicyclo[4.3.0]non-3-ene
2-hydroxymethyl-8-azabicyclo[4.3.0]non-3-ene
2-amino-5-cyclopropyl-8-azabicyclo[4.3.0]non-3-ene
8-azabicyclo[4.3.0]non-2-ene
ethyl 8-azabicyclo[4.3.0]non-4-ene-2-carboxylate
2-hydroxymethyl-8-azabicyclo[4.3.0]non-4-ene
2-amino-8-azabicyclo[4.3.0]non-4-ene
2-ethyloxycarbonylamino-8-azabicyclo[4.3.0]non-4-ene 2-tert-butoxycarbonylamino-8-azabicyclo[4.3.0]non-4-ene
2-benzyloxycarbonylamino-8-azabicyclo[4.3.0]non-4-ene
2-allyloxycarbonylaminomethyl-8-azabicyclo[4.3.0]non-4-ene
2-aminomethyl-8-azabicyclo[4.3.0]non-4-ene
2-ethyloxycarbonylaminomethyl-8-azabicyclo[4.3.0]non-4-ene
2-tert-butoxycarbonylaminomethyl-8-azabicyclo[4.3.0]non-4-ene
2-methylamino-8-azabicyclo[4.3.0]non-4-ene
2-ethylamino-8-azabicyclo[4.3.0]non-4-ene
2-cyclopropylamino-8-azabicyclo[4.3.0]non-4-ene
2-dimethylamino-8-azabicyclo[4.3.0]non-4-ene
2-[(2-hydroxyethyl)-amino]-8-azabicyclo[4.3.0]non-4-ene
2-amino-1-methyl-8-azabicyclo[4.3.0]non-4-ene
2-amino-2-methyl-8-azabicyclo[4.3.0]non-4-ene
2-amino-3-methyl-8-azabicyclo[4.3.0]non-4-ene
2-ethyloxycarbonylamino-3-methyl-8-azabicyclo[4.3.0]non-4-ene
2-tert-butoxycarbonylamino-3-methyl-8-azabicyclo[4.3.0]non-4-ene
2-benzyloxycarbonylamino-3-methyl-8-azabicyclo[4.3.0]non-4-ene
2-allyloxycarbonylaminomethyl-3-methyl-8-azabicyclo[4.3.0]non-4-ene
2-amino-4-methyl-8-azabicyclo[4.3.0]non-4-ene
2-amino-5-methyl-8-azabicyclo[4.3.0]non-4-ene
2-amino-6-methyl-8-azabicyclo[4.3.0]non-4-ene
2-amino-7-methyl-8-azabicyclo[4.3.0]non-4-ene
2-amino-9-methyl-8-azabicyclo[4.3.0]non-4-ene The substituted 8-azabicyclo[4.3.0]non-4-enes and 8-azabicyclo[4.3.0]non-2-ene are the subject-matter of a German application of the Applicant DE-P 4 230 804.6 which is not yet part of the prior art.

Compounds of the general formula (IV)

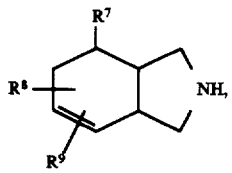
(IV)

in which

R$^7$, R$^8$ and R$^9$ have the meanings given above, are obtained by reacting suitable dienes with suitable dienophiles in a Diels-Alder reaction which can be carried out intermolecularly or intramolecularly, and optionally then carrying out further chemical reactions in order, if appropriate, to synthesize the pyrrolidine ring and in order to introduce substituents desired for the biological action and, as a last step, removing the protective group on the pyrrolidine nitrogen.

When carrying out the Diels-Alder reaction intramolecularly, compounds of the formula (1) or (2)

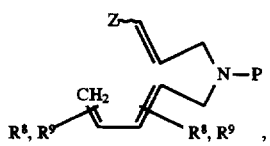
(1)

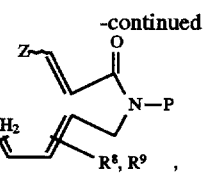
(2)

in which

R$^8$ and R$^9$ have the meaning given above and

P represents a protective group (for example allyl, acyl, carbamoyl or trityl),

Z represents hydrogen, a carboxyl, carboxylic ester or carboxamide group, CN or NO$_2$, are reacted to give compounds of the formula (3) [starting from (1)] or (4) [starting from (2)]

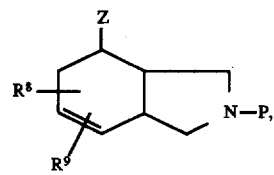
(3)

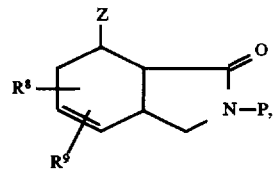
(4)

in which

R$^8$, R$^9$, P and Z have the meanings given above.

Intramolecular Diels-Alder reactions of a similar type are known in some cases: J. M. Mellor, A. M. Wagland; J. Chem. Soc. Perkin I, 997–1005 (1989); W. R. Roush, S. E. Hall; J. Am. Chem. Soc. 103, 5200 (1980); E. Ciganek; Organic Reactions 32, 1–374 (1984). In these publications, however, there are no references to protective groups which are simultaneously suitable for the reaction and can then be removed without problems.

When carrying out the Diels-Alder reaction intermolecularly, dienes of the formula (5) are reacted with dienophiles of the formula (6) to give compounds of the formula (7), and optionally reacted with cyclization to give the lactams of the formula (8) after modification of the groups Z$^1$ and Z$^2$, for example conversion of a cyclic carboxylic anhydride to a diester with removal of the protective groups P$^1$ or P$^1$ and P$^2$.

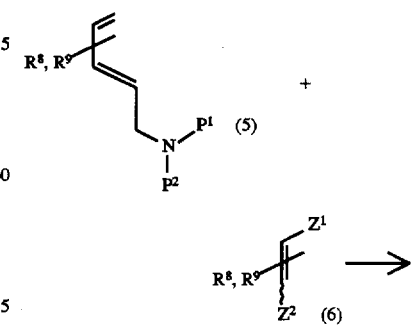

-continued

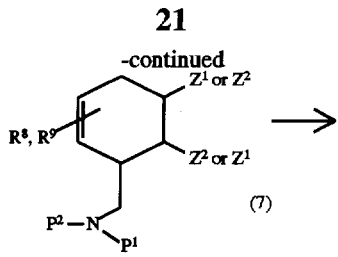

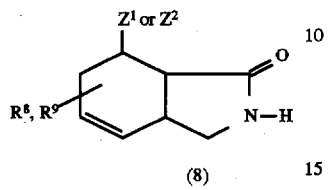

In the formula (5), (6), (7) and (8), $R^8$ and $R^9$ have the meaning given above, $P^1$ represents an acyl or carbamoyl protective group if $P^2$ represents hydrogen or $P^1$ forms an imide together with $P^2$, $Z^1$ and $Z^2$ represent hydrogen, carboxyl, carboxylic ester or carboxamide groups, CN or $NO_2$, where at least one of the two groups $Z^1$ or $Z^2$ must be a carboxylic ester group or a carboxamide group or CN, or $Z^1$ and $Z^2$ together form a bridge such that a cyclic carboxylic anhydride is formed.

Preferred protective groups P, $P^1$, $P^2$ are those protective groups in which, under the conditions which are used for their removal, the cyclization to the lactam and optionally an esterification of a second, still free carboxyl function with the alcohol used as solvent takes place in such a way that all reaction steps can be carried out in a one-pot reaction, and an uncontrolled conversion of optionally diastereomerically and enantiomerically pure starting substances does not take place to isomer mixtures which cannot be separated or are difficult to separate.

Examples which may be mentioned are:

1. the tert-butoxycarbonyl protective group (removal using aqueous or alcoholic acids)
2. the phthalimido protective group (aminolysis using primary amines in aqueous or anhydrous alcohols as solvents)

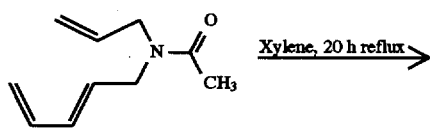

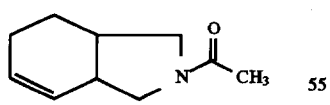

GS: trans = 1:1

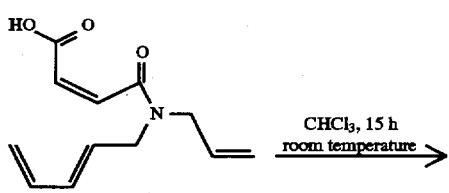

-continued

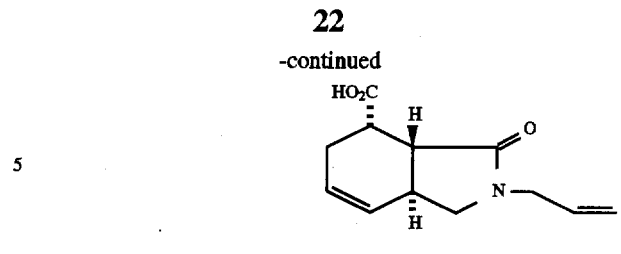

rac. main product

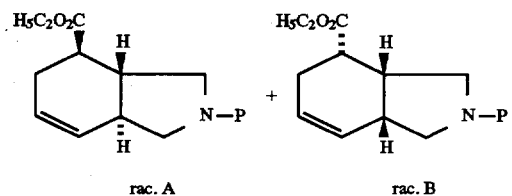

| P | | A:B |
|---|---|---|
| $-H_2C\diagup\diagdown$ | Toluene 15 h reflux | 3:2 |
| 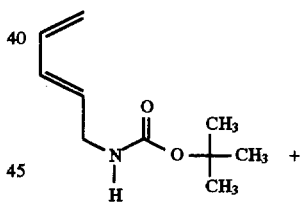 | Toluene 6 h reflux | 4:1 |

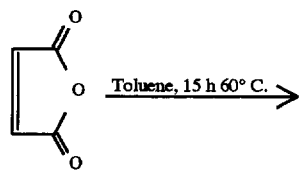 +

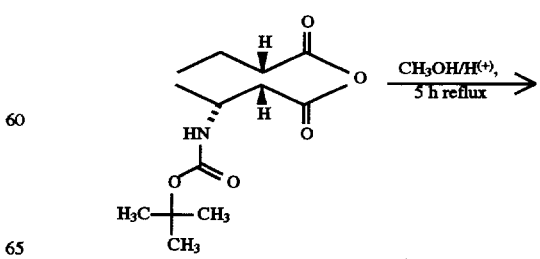

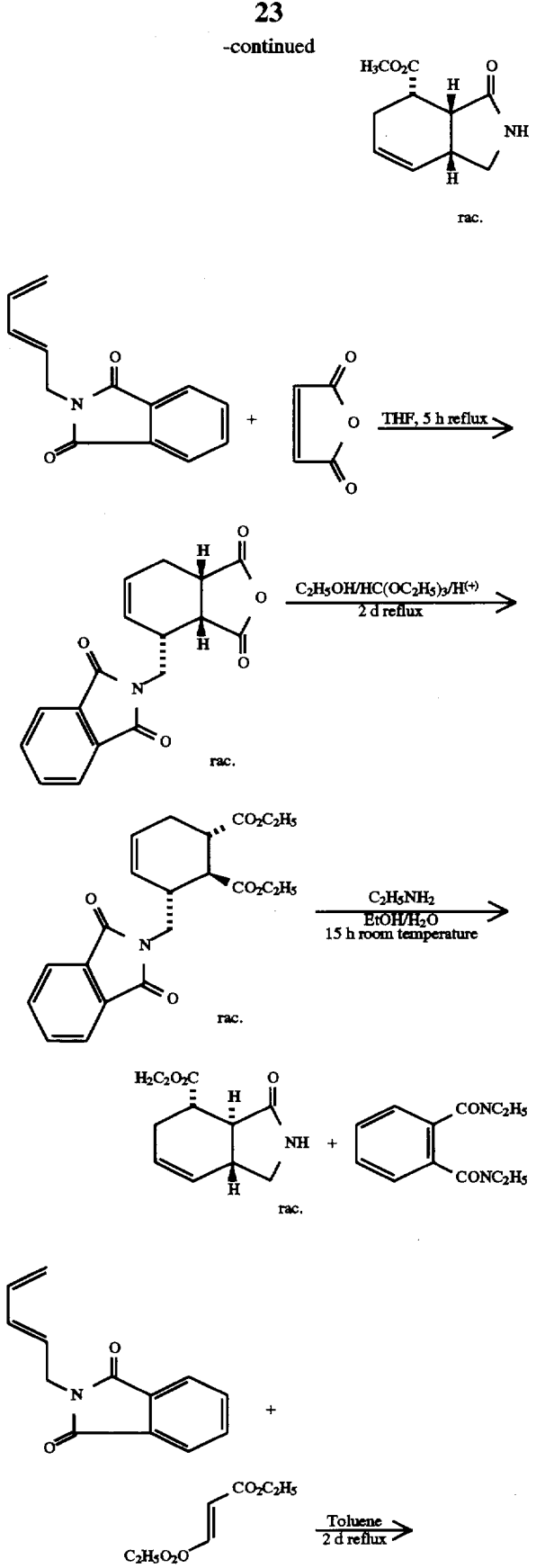
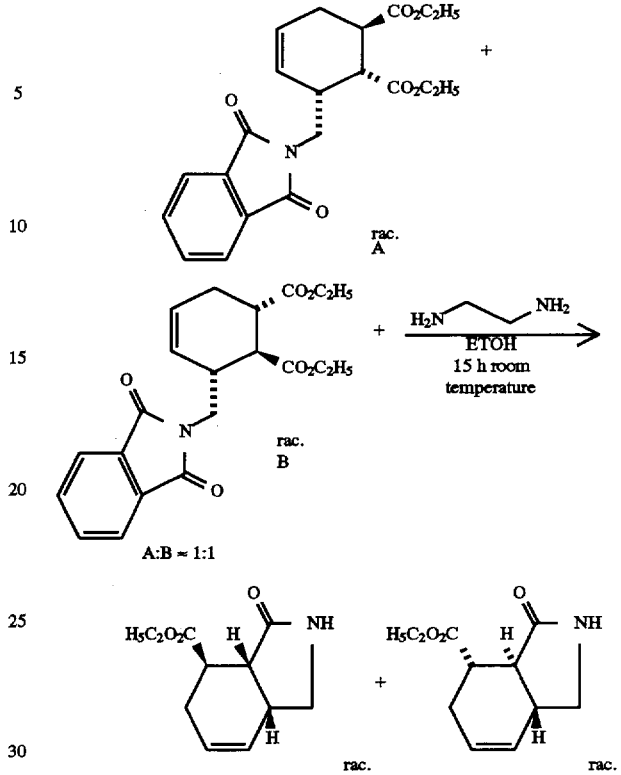

All inert organic solvents are suitable as diluents for the Diels-Alder reaction. These preferably include ethers such as diisopropyl ether, di-n-butyl ether, dimethoxyethane, tetrahydrofuran and anisole, hydrocarbons, such as e.g. hexane, methylcyclohexane, toluene, xylene and mesitylene and halogenated hydrocarbons, such as e.g. chloroform, 1,2-dichloroethane and chlorobenzene. The Diels-Alder reaction, however, can also be carried out without solvent.

The reaction temperatures can be varied within a relatively wide range. In general, the reaction is carried out between about −20° C. and +200° C., preferably between −20° C. and +150° C. The Diels-Alder reaction is normally carried out at normal pressure. To accelerate the reaction, however, pressures up to 1.5 GPa can also be employed.

The further reaction of the compounds of the formula (7) to give the compounds of the formula (8) is carried out as described in the examples or according to known methods of organic chemistry.

In order to obtain the compounds of the formula (III) starting from the compounds of the formula (3), (4) or (8), further reactions are necessary.

Examples which may be mentioned are the hydrolysis of an ester to the carboxylic acid, the reduction of carbonyl groups, for example of esters, to aldehydes or alcohols or of lactam groups to the pyrrolidines, the conversion of a hydroxyl function to an amino function, the conversion of a carboxyl function or one of its derivatives with degradation by one carbon atom to an amine function, the reductive amination of an aldehyde having an amine function present in the molecule, the reductive amination of an aldehyde function present in the molecule using an amine, the introduction of protective groups, the removal of the protective group on the pyrrolidine nitrogen such that further protective groups possibly present in the molecule are retained.

These reactions are carried out as described in the examples or by methods customary in organic chemistry.

The further reaction of the compounds of the formula (3), (4) or (8) to give the compounds of the formula (III) can be illustrated, for example, by the following equations:

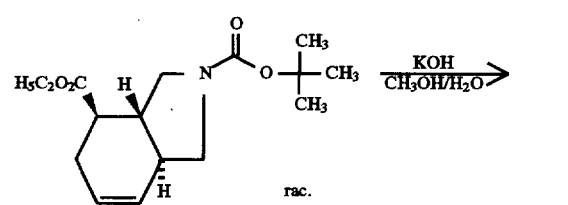

rac.

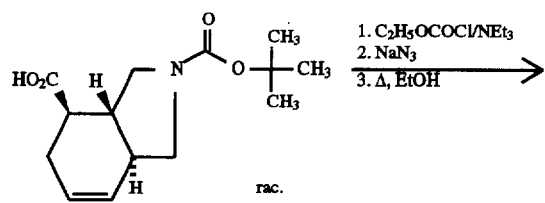

rac.

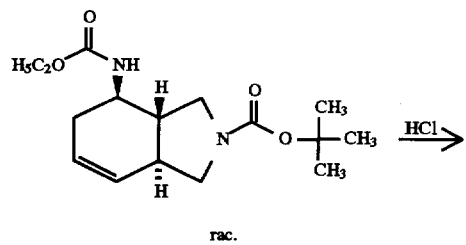

rac.

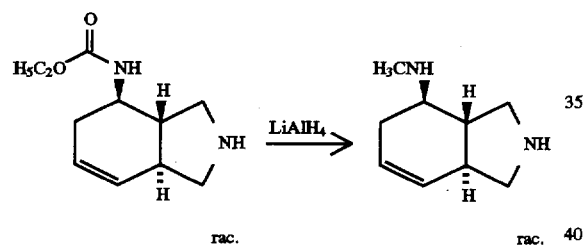

rac.   rac.

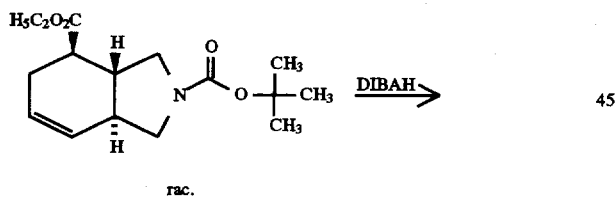

rac.

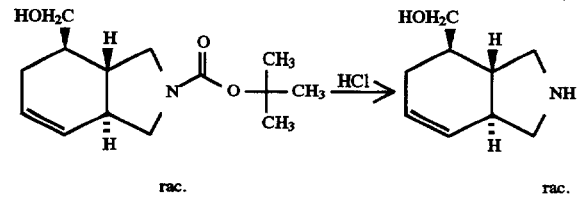

rac.   rac.

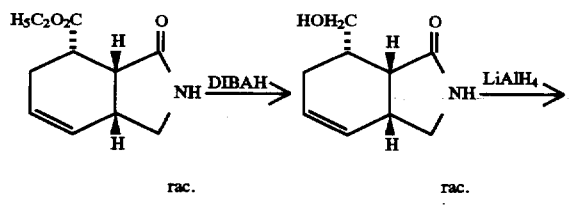

rac.   rac.

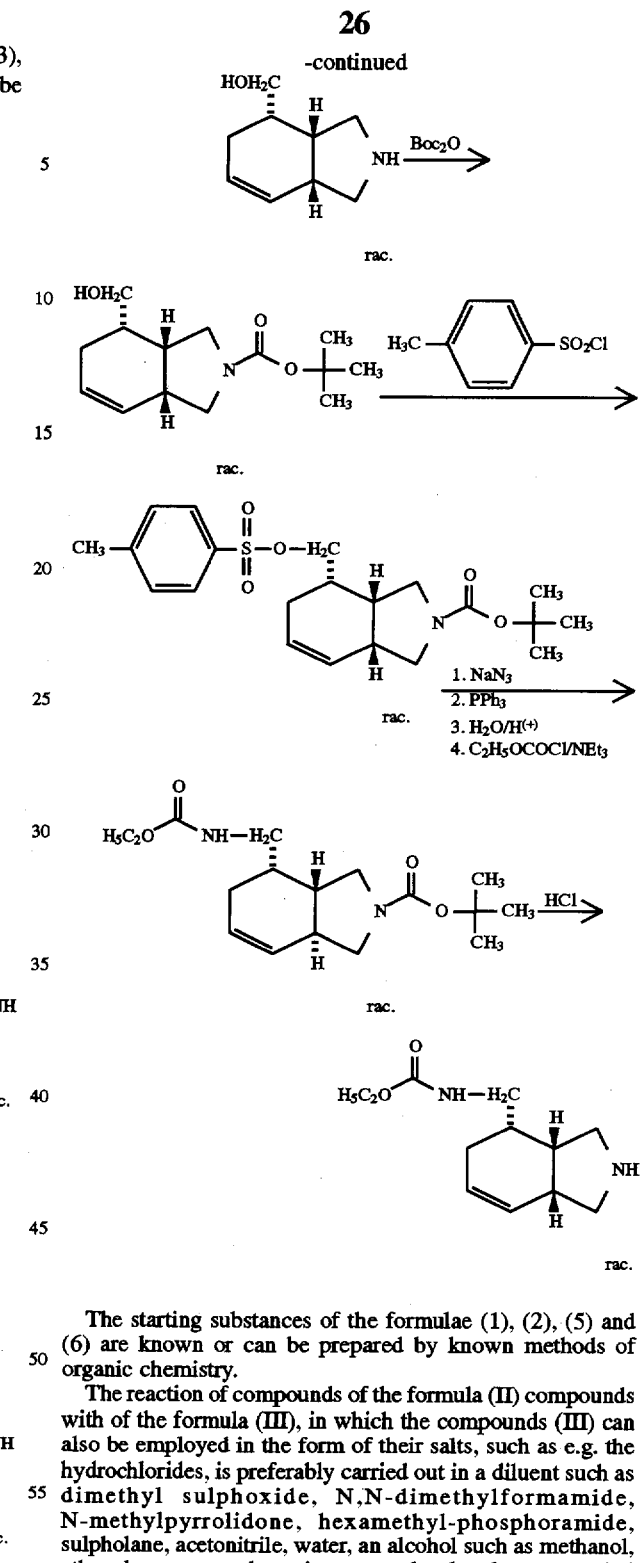

The starting substances of the formulae (1), (2), (5) and (6) are known or can be prepared by known methods of organic chemistry.

The reaction of compounds of the formula (II) compounds with of the formula (III), in which the compounds (III) can also be employed in the form of their salts, such as e.g. the hydrochlorides, is preferably carried out in a diluent such as dimethyl sulphoxide, N,N-dimethylformamide, N-methylpyrrolidone, hexamethyl-phosphoramide, sulpholane, acetonitrile, water, an alcohol such as methanol, ethanol, n-propanol or isopropanol, glycol monomethyl ether or pyridine. Mixtures of these diluents can also be used.

The acid-binding agents used can be all customary inorganic and organic acid-binding agents. These preferably include the alkali metal hydroxides, alkali metal carbonates, organic amines and amidines. The following may be mentioned in detail as being particularly suitable: triethylamine, 1,4-diazabicyclo[2.2.2]octane (DABCO), 1,8-diazabicyclo[5.4.0]undec-7-ene (DBU) or excess amine (III).

The reaction temperatures can be varied within a relatively wide range. In general, the reaction is carried out between about 20° and 200° C., preferably between 80° and 180° C.

The reaction can be carried out at normal pressure, but also at elevated pressure. In general, the reaction is carried out at pressures between 1 bar and 100 bar, preferably between 1 and 10 bar.

When carrying out the process according to the invention, 1 to 15 mol, preferably 1 to 6 mol, of the compound (III) are employed relative to 1 mol of the compound (II).

Free amino groups can be protected during the reaction by a suitable amino protective group, for example by the tert-butoxycarbonyl radical, and liberated again after completion of the reaction by treatment with a suitable acid such as hydrochloric acid or trifluoroacetic acid (see Houben-Weyl, Methoden der Organischen Chemie [Methods of Organic Chemistry], Volume E4, page 144 (1983); J. F. W. Mc Omie, Protective Groups in Organic Chemistry (1973), page 43).

The esters according to the invention are obtained by reaction of an alkali metal salt of the carboxylic acid on which they are based, which can optionally be protected on the N atom by a protective group such as the tert-butoxycarbonyl radical, with suitable halogenoalkyl derivatives in a solvent such as dimethylformamide, dimethylacetamide, N-methylpyrrolidone, dimethyl sulphoxide or tetramethylurea at temperatures of about 0° to 100° C., preferably 0° to 50° C.

The acid addition salts of the compounds according to the invention are prepared in a customary manner, for example by dissolving the betaine in an adequate amount of aqueous acid and precipitating the salt using a water-miscible organic solvent such as methanol, ethanol, acetone or acetonitrile. Equivalent amounts of betaine and acid can also be heated in water or an alcohol such as glycol monoethyl ether and then evaporated to dryness or the precipitated salt filtered off with suction. Pharmaceutically utilizable salts are to be understood as meaning, for example, the salts of hydrochloric acid, sulphuric acid, acetic acid, glycolic acid, lactic acid, succinic acid, citric acid, tartaric acid, methanesulphonic acid, 4-toluenesulphonic acid, galacturonic acid, gluconic acid, embonic acid, glutamic acid or aspartic acid. The compounds according to the invention can also be bound to acidic or basic ion exchangers.

The alkali metal or alkaline earth metal salts of the carboxylic acids according to the invention are obtained, for example, by dissolving the betaine in excess alkali metal or alkaline earth metal hydroxide solution, filtering undissolved betaine and evaporating the filtrate to dryness. Pharmaceutically suitable salts are those of sodium, potassium or calcium. The corresponding silver salts are obtained by reaction of an alkali metal or alkaline earth metal salt with a suitable silver salt such as silver nitrate.

The compounds according to the invention have a strong antibiotic action and exhibit, together with low toxicity, a wide antibacterial spectrum against Gram-positive and Gram-negative microorganisms, in particular even against those which are resistant to various antibiotics, such as e.g. penicillins, cephalosporins, aminoglycosides, sulphonamides and tetracyclines.

These useful properties make possible their use as chemotherapeutic agents in medicine and veterinary medicine and as substances for the preservation of inorganic and organic materials, in particular of organic materials of all types, e.g. polymers, lubricants, dyes, fibres, leather, paper and wood, of foodstuffs and of water.

The compounds according to the invention are active against a very wide spectrum of microorganisms. Gram-negative and Gram-positive bacteria and bacteria-like microorganisms can be controlled using them and the diseases caused by these pathogens prevented, ameliorated and/or cured.

The compounds according to the invention are distinguished by increased action on dormant and resistant microorganisms. In the case of dormant bacteria, i.e. bacteria which exhibit no detectable growth, the compounds act below concentrations of similar substances. This relates not only to the amount to be employed, but also to the rate of destruction. It was possible to observe such results in Gram-positive and -negative bacteria, in particular in *Staphylococcus aureus*, Acinetobacter, *Micrococcus luteus* and *Enterococcus faecalis*.

The compounds according to the invention also exhibit surprising increases in activity against bacteria which are classified as less sensitive in relation to comparable substances, in particular resistant *Staphylococcus aureus* and *Enterococcus faecalis*.

The compounds according to the invention are particularly active against bacteria and bacteria-like microorganisms. They are therefore particularly highly suitable for the prophylaxis and chemotherapy in human and veterinary medicine of local and systemic infectious which are caused by these pathogens.

The compounds are further suitable for the control of protozoonoses and helminthoses.

The active compounds have favourable toxicity to warm-blooded animals and are preferably suitable for the control of bacterial diseases which occur in productive, breeding zoo, laboratory and experimental animals and pets in animal keeping and animal breeding. They are active here against all or individual stages of development and against resistant and normally sensitive strains. By control of the bacterial diseases, illness, cases of death and yield decreases (e.g. in the production of meat, milk, wool, hides, eggs, honey etc.) should be decreased, so that more economical and simple animal keeping is possible as a result of the use of the active compounds.

The productive and breeding animals include mammals such as e.g. cattle, horses, sheep, pigs, goats, camels, water buffalo, donkeys, rabbits, fallow deer, reindeer, fur-bearing animals such as e.g. mink, chinchilla, racoon, birds such as e.g. hens, geese, turkeys, ducks, doves and species of bird for keeping at home and in zoos. They further include productive and ornamental fish.

The laboratory and experimental animals include mice, ram, guinea-pigs, golden hamsters, dogs and cats.

The pets include dogs and cats.

The fish include productive, breeding, aquarium and ornamental fish of all ages, which live in fresh and salt water. The productive and breeding fish include e.g. carp, eel, trout, whitefish, salmon, bream, roach, rudd chub, sole, plaice, halibut, Japanese yellowtail (*Seriola quinqueradiata*), Japanese eel (*Anguilla japonica*), red seabream (*Pagurus major*), sea bass (*Dicentrarchus labrax*), grey mullet (*Mugilus cephalus*), pompano, gilthread seabream (*Spares auratus*), Tilapia spp., Chichlidae species such as e.g. Plagioscion, channel catfish, The agents according to the invention are particularly suitable for the treatment of fry, e.g. carp of 2–4 cm body length. The agents are also very highly suitable in eel breeding.

Administration can be carried out both prophylactically and therapeutically.

Administration of the active compounds is carried out directly or enterally, parenterally, dermally or nasally in the form of suitable preparations.

Enteral administration of the active compounds is carried out e.g. orally in the form of powders, suppositories, tablets, capsules, pastes, drinks, granules, drenches, boli, medicated feed or drinking water. Dermal administration is carried out e.g. in the form of dipping, spraying, bathing, washing, pouring-on and spotting-on and dusting. Parenteral administration is carried out e.g. in the form of injection (intramuscular, subcutaneous, intravenous, intraperitoneal) or by implants.

Suitable preparations are:

solutions such as injection solutions, oral solutions, concentrates for oral administration after dilution, solutions for use on the skin or in body cavities, pour-on formulations, gels;

emulsions and suspensions for oral or dermal administration and for injection; Semi-solid preparations;

formulation in which the active compound is processed in an ointment base or in an oil-in-water or water-in-oil emulsion base;

solid preparations such as powders, premixes or concentrates, granules, pellets, tablets, boli, capsules; aerosols and inhalants, active compound-containing moulded articles.

Injection solutions are administered intravenously, intramuscularly and subcutaneously.

Injection solution are prepared by dissolving the active compound in a suitable solvent and possibly adding additives such as solubilizers, acids, bases, buffer salts, antioxidants or preservatives. The solutions are sterile-filtered and bottled.

Solvents which may be mentioned are: physiologically tolerable solvents such as water, alcohols such as ethanol, butanol, benzyl acohol, glycerol, hydrocarbons, propylene glycol, polyethylene glycols, N-methyl-pyrrolidone, and mixtures thereof.

The active compounds can optionally also be dissolved in physiologically tolerable vegetable or synthetic oils which are suitable for injection.

Solubilizers which may be mentioned are: solvents which promote the solution of the active compound in the main solvent or prevent its precipitation. Examples are polyvinylpyrrolidone, polyethoxylated castor oil, polyethoxylated sorbitan esters.

Preservatives are: benzyl alcohol, trichlorobutanol, p-hydroxybenzoic acid esters, n-butanol.

Oral solutions are administered directly. Concentrates are administered orally after prior dilution to the administration concentration. Oral solutions and concentrates are prepared as described above under the injection solutions, it being possible to dispense with sterile operation.

Solutions for use on the skin are applied in drops, spread on, robbed in, sprayed on, splashed on or applied by dipping, bathing or washing. These solutions are prepared as described above under the injection solutions.

It may be advantageous to add thickening agents during preparation. Thickening agents are: Inorganic thickening agents such as bentonites, colloidal silica, aluminium monostearate, organic thickening agents such as cellulose derivatives, polyvinyl alcohols and their copolymers, acrylates and metacrylates.

Gels are applied to or spread on the skin or introduced into body cavities. Gels are prepared by treating solutions which have been prepared as described under the injection solutions with an amount of thickening agent such that a clear material having an ointment-like consistency results. The thickening agents employed are the thickening agents given further above.

Pouring-on formulations are poured onto or sprayed onto restricted areas of the skin, the active compound either penetrating the skin and acting systemically or being distributed on the body surface.

Pouring-on formulations are prepared by dissolving suspending or emulsifying the active compound in suitable skin-compatible solvents or solvent mixtures. Other auxiliaries such as colorants, absorption-promoting substances, antioxidants, light screens or adhesives are optionally added.

Solvents which may be mentioned are: water, alkanols, glycols, polyethylene glycols, polypropylene glycols, glycerol, aromatic alcohols such as benzyl alcohol, phenylethanol, phenoxyethanol, esters such as ethyl acetate, butyl acetate, benzyl benzoate, ethers such as alkylene glycol alkyl ethers such as dipropylene glycol monomethyl ether, diethylene glycol monobutyl ether, ketones such as acetone, methyl ethyl ketone, aromatic and/or aliphatic hydrocarbons, vegetable or synthetic oils, DMF, dimethylacetamide, N-methylpyrrolidone or 2-dimethyl-4-oxymethylene-1,3-dioxolane.

Colorants are all colorants permitted for use on animals and which can be dissolved or suspended.

Absorption-promoting substances are e.g. DMSO, spreading oils such as isopropyl myristate, dipropylene glycol pelargonate, silicone oils, fatty acid esters, triglycerides or fatty alcohols.

Antioxidants are sulphites or metabisulphites such as potassium metabisulphite, ascorbic acid, butylhydroxytoluene, butylhydroxyanisole and tocopherol.

Light screens are e.g. substances of the benzophenone class or novantisolic acid.

Adhesives are e.g. cellulose derivatives, starch derivatives, polyacrylates, natural polymers such as alginates, and gelatine.

Emulsions can be administered orally, dermally or as injections.

Emulsions are either of the water-in-oil type or of the oil-in-water type.

They are prepared by dissolving the active compound either in the hydrophobic or in the hydrophilic phase and homogenizing this with the solvent of the other phase with the aid of suitable emulsifiers and optionally other auxiliaries such as colorants, absorption-promoting substances, preservatives, antioxidants, light screens and viscosity-increasing substances.

Hydrophobic phases (oils) which may be mentioned are: paraffin oils, silicone oils, natural vegetable oils such as sesame oil, almond oil, castor oil, synthetic triglycerides such as caprylic/capric acid biglyceride, triglyceride mixture with vegetable fatty acids of chain length $C_{8-12}$ or other specially selected natural fatty acids, partial glyceride mixtures of saturated or unsaturated fatty acids possibly also containing hydroxyl groups, mono- and diglycerides of $C_8/C_{10}$-fatty acids.

Fatty acid esters such as ethyl stearate, di-n-butyryl adipate, hexyl laurate, dipropylene glycol pelargonate, esters of a branched fatty acid of medium chain length containing saturated fatty alcohols of chain length $C_{16}$–$C_{18}$, isopropyl myristate, isopropyl palmitate, caprylic/capric acid esters of saturated fatty alcohols of chain length $C_{12}$–$C_{18}$, isopropyl stearate, oleyl oleate, decyl oleate, ethyl oleate, ethyl lactate, waxy fatty acid esters such as dibutyl phthalate, diisopropyl adipate, ester mixtures related to the latter, inter alia fatty alcohols such as isotridecyl alcohol, 2-octyldodecanol, cetylstearyl alcohol and oleyl alcohol.

Fatty acids such as e.g. oleic acid and their mixtures.

Hydrophilic phases which may be mentioned are: water, alcohols such as e.g. propylene glycol, glycerol, sorbitol and their mixtures.

Emulsifiers which may be mentioned are: non-ionic surfactants, e.g. polyethoxylated castor oil, polyethoxylated sorbitan monooleate, sorbitan monostearate, glyceryl monostearate, polyoxyethyl stearate, alkylphenol polyglycol ether;

ampholytic surfactants such as di-Na N-lauryl-β-iminodipropionate or lecithin;

anionic surfactants, such as Na laurylsulphate, fatty alcohol ether sulphates, mono/dialkyl polyglycol ether orthophosphoric acid ester monoethanolamine salt; cationic surfactants such as cetyltrimethylammonium chloride.

Other auxiliaries which may be mentioned are: viscosity-increasing and emulsion-stabilizing substances such as carboxymethylcellulose, methylcellulose and other cellulose and starch derivatives, polyacrylates, alginates, gelating gum arabic, polyvinylpyrrolidone, polyvinyl alcohol, copolymers of methyl vinyl ether and maleic anhydride, polyethylene glycols, waxes, colloidal silica or mixtures of the substances mentioned.

Suspensions can be administered orally, dermally or as an injection. They are prepared by suspending the active compound in a vehicle, optionally with the addition of other auxiliaries such as wetting agents, colorants, absorption-promoting substances, preservatives, antioxidants light screens.

Vehicles which may be mentioned are all homogeneous solvents and solvent mixtures.

Wetting agents (dispersing agents) which may be mentioned are the surfactants given further above.

Further auxiliaries which may be mentioned are those given further above.

Semi-solid preparations can be administered orally or dermally. They differ from the suspensions and emulsions described above only by their higher viscosity.

For the production of solid preparations, the active compound is mixed with suitable excipients, optionally with the addition of auxiliaries, and brought into the desired form.

Excipients which may be mentioned are all physiologically tolerable solid inert substances. All such serve inorganic and organic substances. Inorganic substances are e.g. sodium chloride, carbonates such as calcium carbonate, hydrogen carbonates, aluminas, silicic acids, clays, precipitated or colloidal silica, phosphates.

Organic substances are e.g. sugar, cellulose, foodstuffs and feeds such as milk powder, animal meals, cereal flours and meals, starches.

Auxiliaries are preservatives, antioxidants and colorants which have already been mentioned above.

Other suitable auxiliaries are lubricants and glidants such as e.g. magnesium stearate, stearic acid, talc, bentonites, disintegration-promoting substances such as starch or crosslinked polyvinylpyrrolidone, binding agents such as e.g. starch, gelatine or linear polyvinylpyrrolidone, and dry binding agents such as microcrystalline cellulose.

The active compounds can also be present in the preparations in a mixture with synergists or with other active compounds.

Ready-for-use preparations contain the active compound in concentrations of 10 ppm–20 per cent by weight, preferably of 0.1–10 per cent by weight.

Preparation which are diluted before use contain the active compound in concentrations of 0.5–90 per cent by weight, preferably of 1 to 50 per cent by weight.

In general, it has proven advantageous to administer amounts of about 0.5 to about 50 mg, preferably 1 to 20 mg, of active compound per kg of body weight per day to achieve effective results.

The active compounds can also be administered together with the feed or drinking water of the animals.

Feeds and foodstuffs contain 0.01 to 100 ppm, preferably 0.5 to 50 ppm, of the active compound in combination with a suitable edible material.

Such a feed and foodstuff can be used both for curative purposes and for prophylactic purposes.

Such a feed or foodstuff is prepared by mixing a concentrate or a premix which contains 0.5 to 30%, preferably 1 to 20% by weight, of an active compound in a mixture with an edible organic or inorganic carrier with customary feeds. Edible carriers are e.g. maize flour or maize and soya bean flour or mineral salts which preferably contain a small amount of an edible dust-preventing oil, e.g. maize oil or soya oil. The premix obtained in this process can then be added to the complete feed before feeding it to the animals.

The minimum inhibitory concentrations (MIC) of the compounds according to the invention were determined by serial dilution methods on Iso-Sensitest agar (Oxoid). For each test substance, a series of agar plates was prepared which contained decreasing concentrations of the active compound at, in each case, double dilution. The agar plates were inoculated with a multipoint inoculator (Denley). For inoculation, overnight cultures of the pathogens were reed which had previously been diluted such that each inoculation point contained about $10^4$ colony-forming particles. The inoculated agar plates were incubated at 37° C., and the growth of microorganism was read off after about 20 hours. The MIC value (μg/ml) indicates the lowest active compound concentration at which no growth was to be detected with the naked eye.

The MIC values of some of the compounds according to the invention are shown in the table below.

TABLE

| | | MIC values | | | |
|---|---|---|---|---|---|
| | | Example No. | | | |
| Species | Strain | 4 | 5 | 7 | 11 |
| E. coli | Neumann | 0.03 | ≦0.015 | ≦0.015 | ≦0.015 |
| | ATCC 25922 | 0.03 | ≦0.015 | ≦0.015 | ≦0.015 |
| Klebsiella pneumoniae | 8085 | 0.06 | 0.03 | 0.03 | ≦0.015 |
| | 63 | 0.06 | 0.03 | 0.03 | ≦0.015 |
| Providencia sp. | 12012 | 0.06 | ≦0.015 | 0.03 | ≦0.015 |
| | 12052 | 4 | 2 | 2 | 16 |
| Micrococcus luteus | 9341 | ≦0.015 | ≦0.015 | ≦0.015 | 0,5 |
| Staphylococcus aureus | ICB 25701 | 0.5 | 0.125 | 0.25 | 0.5 |
| | ATCC 29213 | ≦0.015 | ≦0.015 | ≦0.015 | ≦0.015 |
| | 133 | ≦0.015 | ≦0.015 | ≦0.015 | ≦0.015 |
| | ICB 25768 | 1 | 0.25 | 0.5 | 16 |
| Enterococcus faecalis | 27101 | 0.06 | 0.03 | ≦0.015 | ≦0.015 |
| | 9790 | 0.06 | 0.03 | 0.03 | ≦0.015 |
| Acinetobacter | 14068 | ≦0.015 | ≦0.015 | ≦0.015 | ≦0.015 |

Preparation of the Active Compounds

EXAMPLE 1

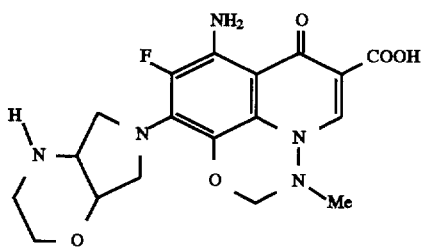

8-Amino-9-fluoro-3-methyl-10-(2-oxa-5,8-diazabicyclo[4.3.0]nonan-8-yl)-7-oxo-2,3-dihydro-7H-pyrido[1,2,3-d,e][1,3,4]benzoxadiazine-6-carboxylic acid 100 mg (0.336 mmol) of 8-amino-9,10-difluoro-3-methyl-7-oxo-2,3-dihydro-7H-pyrido[1,2,3-d,e][1,3,4]-benzoxadiazine-6-carboxylic acid are heated at 110° C. under argon for six hours with 86 mg (0.671 mmol) of 2-oxa-5,8-diazabicyclo[4.3.0]nonane in 3 ml of pyridine. The mixture is concentrated in a high vacuum, and the residue is recrystallized from ethanol and dried.

Yield: 102 mg (72% of theory)

Melting point: 295°–296° C.

EXAMPLE 2

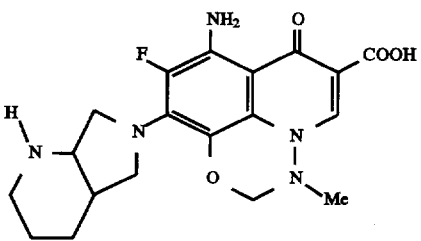

8-Amino-10-(2,8-diazabicyclo[4.3.0]nonan-8-yl)-9-fluoro-3-methyl-7-oxo-2,3-dihydro-7H-pyrido[1,2,3-d,e][1,3,4]benzoxadiazine-6-carboxylic acid 100 mg (0.336 mmol) of 8-amino-9,10-difluoro-3-methyl-7-oxo-2,3-dihydro-7H-pyrido[1,2,3-d,e][1,3,4] benzoxadiazine-6-carboxylic acid are heated at 120° C. under argon for two hours with 127 mg (1.01 mmol) of 2,8-diazabicyclo[4.3.0]nonane in 3 ml of dimethyl sulphoxide (DMSO). The mixture is concentrated in a high vacuum, and the residue is recrystallized from ethanol and dried.

Yield: 99 mg (73% of theory)

Melting point: 284° C. (with decomposition)

EXAMPLE 3

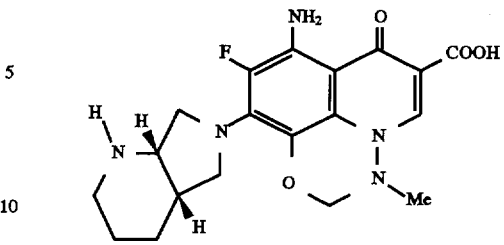

8-Amino-10-((1S,6S)-2,8-diazabicyclo[4.3.0]nonan-8-yl)-9-fluoro-3-methyl-7-oxo-2,3-dihydro-7H-pyrido[1,2,3-d,e][1,3,4]benzoxadiazine6-carboxylic acid 100 mg (0.336 mmol) of 8-amino-9,10-difluoro-3-methyl-7-oxo-2,3-dihydro-7H-pyrido[1,2,3-d,e][1,3,4] benzoxadiazine-6-carboxylic acid are heated at 130° C. under argon for two hours with 85 mg (0.674 mmol) of (1S,6S)-2,8-diazabicyclo[4.3.0]nonane in 3 ml of dimethyl sulphoxide (DMSO). The mixture is concentrated in a high vacuum, and the residue is recrystallized from ethanol and dried.

Yield: 101 mg (74% of theory)

Melting point: >300° C. (with decomposition)

EXAMPLE 4

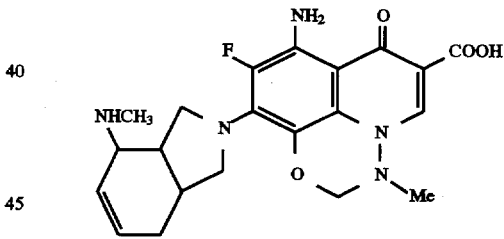

8-Amino-9-fluoro-3-methyl-10-(2-methylamino-8-azabicyclo[4.3.0]non-3-en-8-yl)-7-oxo-2,3-dihydro-7H-pyrido[1,2,3-d,e][1,3,4]benzoxadiazine-6-carboxylic acid 200 mg (0.673 mmol) of 8-amino-9,10-difluoro-3-methyl-7-oxo-2,3-dihydro-7H-pyrido[1,2,3-de][1,3,4] benzoxadiazine-6-carboxylic acid are heated at 130° C. under argon for three hours with 200 mg (1.31 mmol) of 2-methylamino-8-azabicyclo[4.3.0]non-3-ene in 6 ml of DMSO. The mixture is concentrated in a high vacuum, and the residue is recrystallized from ethanol and dried.

Yield: 274 mg (95% of theory)

Melting point: 256° C.

EXAMPLE 5

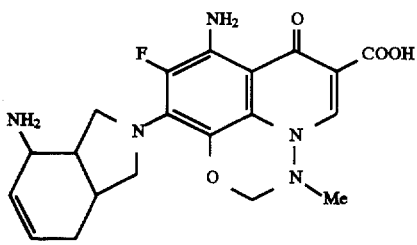

8-Amino-10-(2-amino-8-azabicyclo[4.3.0]non-3-en-8-yl)-9-fluoro-3-methyl-7-oxo-2,3-dihydro-7H-pyrido[1,2,3-d,e][1,3,4]benzoxadiazine-6-carboxylic acid 200 mg (0.673 mmol) of 8-amino-9,10-difluoro-3-methyl-7-oxo-2,3-dihydro-7H-pyrido[1,2,3-de][1,3,4]benzoxadiazine-6-carboxylic acid are heated at 120° C. under argon for two hours with 186 mg (1.35 mmol) of 2-amino-8-azabicyclo[4.3.0]non-3-ene in 6 ml of DMSO. The mixture is concentrated in a high vacuum, and the residue is recrystallized from ethanol and dried.

Yield: 193 mg (69% of theory)

Melting point: 274°–275° C.

EXAMPLE 6

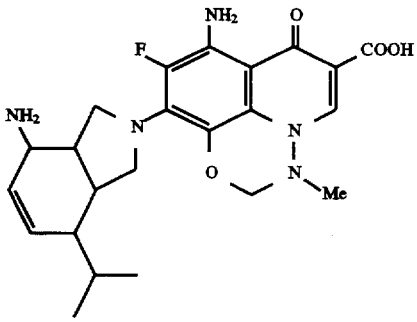

8-Amino-10-(2-amino-5-isopropyl-8-azabicyclo[4.3.0]non-3-en-8-yl)-9-fluoro-3-methyl-7-oxo-2,3-dihydro-7H-pyrido[1,2,3-d,e][1,3,4]benzoxadiazine-6-carboxylic acid 100 mg (0.336 mmol) of 8-amino-9,10-difluoro-3-methyl-7-oxo-2,3-dihydro-7H-pyrido[1,2,3-de][1,3,4]benzoxadiazine-6-carboxylic acid are heated at 130° C. under argon for two hours with 121 mg (0.671 mmol) of 2-amino-5-isopropyl-8-azabicyclo[4.3.0]non-3-ene in 3 ml of DMSO. The mixture is concentrated in a high vacuum, and the residue is recrystallized from ethanol and dried.

Yield: 69 mg (45% of theory)

Melting point: 227° C.

EXAMPLE 7

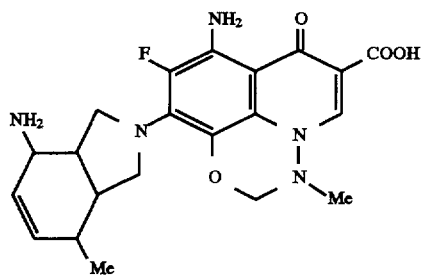

8-Amino-10-(2-amino-5-methyl-8-azabicyclo[4.3.0]non-3-en-8-yl)-9-fluoro-3-methyl-7-oxo-2,3-dihydro-7-H-pyrido[1,2,3-d,e][1,3,4]benzoxadiazine-6-carboxylic acid 200 mg (0.673 mmol) of 8-amino-9,10-difluoro-3-methyl-7-oxo-2,3-dihydro-7H-pyrido[1,2,3-d,e][1,3,4]benzoxadiazine-6-carboxylic acid are heated at 100° C. under argon for five hours with 205 mg (1.35 mmol) of 2-amino-5-methyl-8-azabicyclo[4.3.0]non-3-ene in 6 ml of pyridine. The mixture is concentrated in a high vacuum, and the residue is recrystallized from ethanol and dried.

Yield: 233 mg (81% of theory)

Melting point: 225° C.

EXAMPLE 8

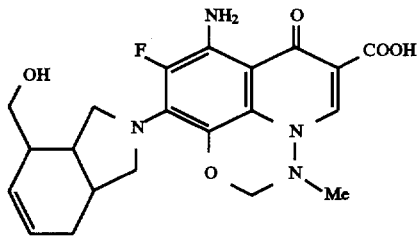

8-Amino-10-(2-hydroxymethyl-8-azabicyclo[4.3.0]non-3-en-8-yl)-9-fluoro-3-methyl-7-oxo-2,3-dihydro-7H-pyrido[1,2,3-d,e][1,3,4]benzoxadiazine-6-carboxylic acid 100 mg (0.336 mmol) of 8-amino-9,10-difluoro-3-methyl-7-oxo-2,3-dihydro-7H-pyrido[1,2,3-d,e][1,3,4]benzoxadiazine-6-carboxylic acid are heated at 130° C. under argon for three hours with 103 mg (0.672 mmol) of 2-hydroxymethyl-8-azabicyclo[4.3.0]non-3-ene in 3 ml of DMSO. The mixture is concentrated in a high vacuum, and the residue is recrystallized from ethanol and dried.

Yield: 105 mg (73% of theory)

Melting point: 278°–280° C.

EXAMPLE 9

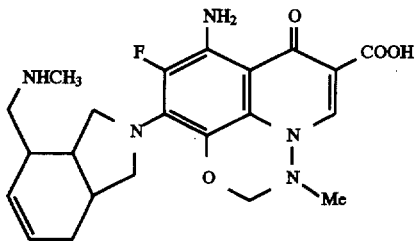

8-Amino-10-(2-methylaminomethyl-8-azabicyclo[4.3.0]non-3-en-8-yl)-9-fluoro-3-methyl-7-oxo-2,3-dihydro-7H-pyrido[1,2,3-d,e][1,3,4]benzoxadiazine-6-carboxylic acid 100 mg (0.336 mmol) of 8-amino-9,10-difluoro-3-methyl-7-oxo-2,3-dihydro-7H-pyrido[1,2,3-d,e][1,3,4]benzoxadiazine-6-carboxylic acid are heated at 110° C. under argon for fourteen hours with 112 mg (0.673 mmol) of 2-methylaminomethyl-8-azabicyclo[4.3.0]non-3-ene in 3 ml of pyridine. The mixture is concentrated in a high vacuum, and the residue is recrystallized from ethanol and dried.

Yield: 136 mg (91% of theory)

Melting point: 250° C.

EXAMPLE 10

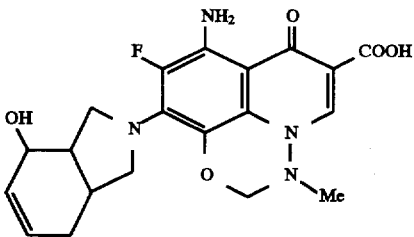

8-Amino-10-(2-hydroxy-8-azabicyclo[4.3.0]non-3-en-8-yl)-9-fluoro-3-methyl-7-oxo-2,3-dihydro-7H-pyrido[1,2,3-d,e][1,3,4]benzoxadiazine-6-carboxylic acid 100 mg (0.336 mmol) of 8-amino-9,10-difluoro-3-methyl-7-oxo-2,3-dihydro-7H-pyrido[1,2,3-d,e][1,3,4]benzoxadiazine-6-carboxylic acid are heated at 120° C. under argon for four hours with 94 mg (0.675 mmol) of 2-hydroxy-8-azabicyclo[4.3.0]non-3-ene in 3 ml of DMSO. The mixture is concentrated in a high vacuum, and the residue is recrystallized from ethanol and dried.

Yield: 83 mg (59% of theory)

Melting point: >300° C. (with decomposition)

EXAMPLE 11

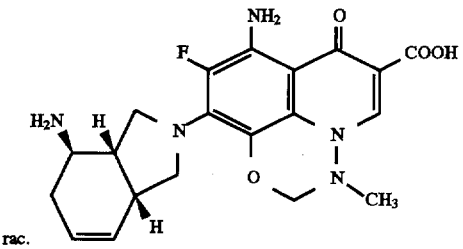

8-Amino-10-((1SR,2RS,6RS)-2-amino-8-azabicyclo[4.3.0]non-4-en-8-yl)-9-fluoro-3-methyl-7-oxo-2,3-dihydro-7H-pyrido[1,2,3-d,e][1,3,4]benzoxadiazine-6-carboxylic acid 90 mg (0.303 mmol) of 8-amino-9,10-difluoro-3-methyl-7-oxo-2,3-dihydro-7H-pyrido[1,2,3-d,e][1,3,4]benzoxadiazine-6-carboxylic acid are heated at 60° C. under nitrogen for seven hours with 54 mg (0.391 mmol) of (1SR,2RS,6RS)-2-amino-8-azabicyclo[4.3.0]non-4-ene in 10 ml of pyridine. The mixture is concentrated in a high vacuum, and the residue is recrystallized from ethanol and dried.

Yield: 120 mg (96% of theory)

Melting point: >300° C.

EXAMPLE 12

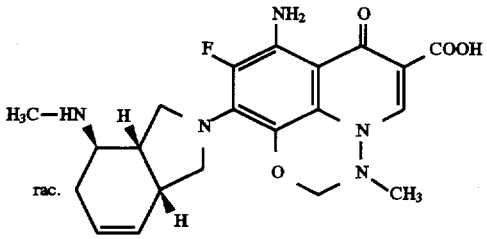

8-Amino-9-fluoro-3-methyl-10-((1SR,2RS,6RS)-2-methylamino-8-azabicyclo[4.3.0]-non-4-en-8-yl)-7-oxo-2,3-dihydro-7H-pyrido[1,2,3-d,e][1,3,4]benzoxadiazine-6-carboxylic acid 445 mg (1.5 mmol) of 8-amino-9,10-difluoro-3-methyl-7-oxo-2,3-dihydro-7H-pyrido[1,2,3-d,e][1,3,4]benzoxadiazine-6-carboxylic acid and 295 mg (1.95 mmol) of (1SR,2RS,6RS)-2-methylamino-8-azabicyclo[4.3.0]non-4-ene (the product of Example N) are reacted, as described in Example 11.

Yield: 540 mg (84% of theory).

Melting point: 292° C. (with decomposition).

EXAMPLE 13

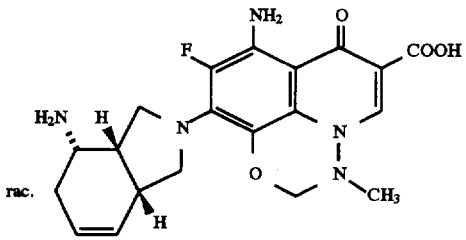

8-Amino-10-((1SR,2SR,6RS)-2-amino-8-azabicyclo[4.3.0]non-4-en-8-yl)-9-fluoro-3-methyl-7-oxo-2,3-dihydro-7H-pyrido[1,2,3-d,e][1,3,4]benzoxadiazine-6-carboxylic acid 445 mg (1.5 mmol) of 8-amino-9,10-difluoro-3-methyl-7-oxo-2,3-dihydro-7H-pyrido-[1,2,3-d,e][1,3,4]benzoxadiazine-6-carboxylic acid and 270 mg (1.95 mmol) of (1SR, 2SR, 6RS)-2-amino-8-azabicyclo[4.3.0]non-4-ene are reacted, as described in Example 11.

Yield: 490 mg (79% of theory)

Melting point: 246° C. (with decomposition)

EXAMPLE 14

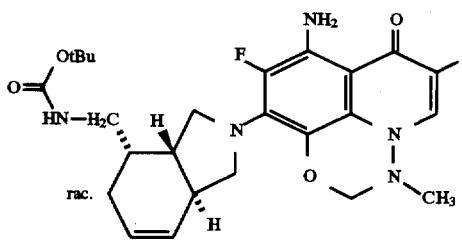

8-Amino-9-fluoro-3-methyl-7-oxo-10-((1SR, 2SR, 6SR)-2-(tert.-butyloxy-carbonyl)aminomethyl-8-azabicyclo[4.3.0]non-4-en-8-yl)-2,3-dihydro-7H-pyrido[1,2,3-d,e][1,3,4]benzoxadiazine-6-carboxylic acid 370 mg (1.25 mmol) of 8-amino-9,10-diluoro-3-methyl-7-oxo-2,3-dihydro-7H-pyrido-[1,2,3-d,e][1,3,4]benzoxadiazine-6-carboxylic acid and 410 mg (1.6 mmol) of (1SR, 2SR, 6RS )-2-(tert.-butyloxycarbonyl)aminomethyl-8-azabicyclo[4.3.0]non-4-ene are reacted, as described in Example 11.

Yield: 470 mg (71% of theory)

Melting point: 227° C. (with decomposition)

EXAMPLE 15

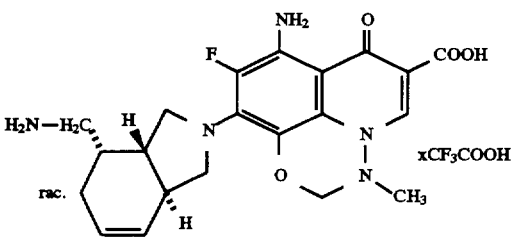

The trifluoroacetic acid salt of 8-Amino-10-((1SR, 2SR, 6SR)-2-aminomethyl-8-azabicyclo[4.3.0]non-4-en-8yl)-9-fluoro-3-methyl-7-oxo-2,3-dihydro-7H-pyrido[1,2,3-d,e][1,3,4]benzoxadiazine-6-carboxylic acid 400 mg (0.75 mmol) of the product of Example 14 are suspended in 10 ml of ice-cooled trifluoroacetic acid. The mixture is heated to room temperature over a period of one hour, a clear solution being formed. After adding methanol the precipitated product is filtered off by suction and dried in a drying cabinet at 50° C.

Yield: 400 mg (quantitative)

Melting point: 235° C. (with decomposition)

EXAMPLE 16

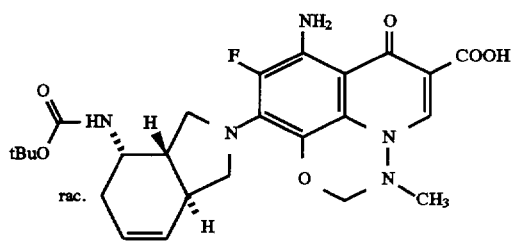

8-Amino-2-(tert.-butyloxycarbonyl)amino-8-azabicyclo[4.3.0]non-4-en-8-yl)-9-fluoro-3-methyl-7-oxo-10-((1SR,2SR,6SR)-2,3-dihydro-7H-pyrido[1,2,3-d,e][1,3,4]benzoxadiazine-6-carboxylic acid 595 mg (2.0 mmol) of 8-amino-9,10-difluoro-3-methyl-7-oxo-2,3-dihydro-7H-pyrido[1,2,3-d,e][1,3,4]benzoxadiazine-6-carboxylic acid and 620 mg (2.6 mmol) of (1SR, 2SR, 6RS)-2-(tert.-butyloxycarbonyl)amino-8-azabicyclo[4.3.0]non-4-ene are reacted, as described in Example 11.

Yield: 850 mg (82% of theory)

Melting point: 259° C. (with decomposition).

EXAMPLE 17

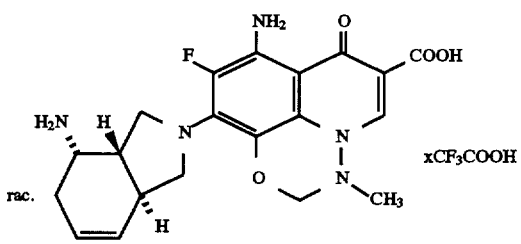

The trifluoroacetic acid salt of 8-amino-10-((1SR, 2SR, 6SR)-2-amino-8-azabicyclo[4.3.0]non-4-en-8-yl)-9-fluoro-3-methyl-7-oxo-2,3-dihydro-7H-pyrido[1,2,3-d,e][1,3,4]benzoxadiazine-6-carboxylic acid The product of Example 16 (700 mg; 1.3 mmol) is reacted with trifluoroacetic acid, as described in Example 16.

Yield: 600 mg (90% of theory).

Melting point: 258° C. (with decomposition).

EXAMPLE 18

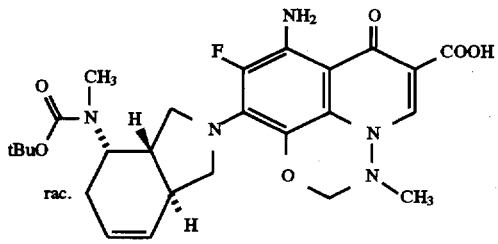

8-Amino-2-(N-tert.-butyloxycarbonyl-N-methyl)amino-8-azabicyclo[4.3.0]non-4-en-8-yl)-9-fluoro-3-methyl-7-oxo-10-((1SR,2SR,6SR)-2,3-dihydro-7H-pyrido[1,2,3-d,e][1,3,4]benzoxadiazine-6-carboxylic acid 595 mg (2.3 mmol) of 8-amino-9,10-difluoro-3-methyl-7-oxo-2,3-dihydro-7H-pyrido[1,2,3-d,e][1,3,4] benzoxadiazine-6-carboxylic acid and 755 mg (3.0 mmol) of (1SR, 2SR, 6RS)-2-(N-tert.-butyloxycarbonyl-N-methyl)amino-8-azabicyclo[4.3.0]non-4-ene are reacted, as described in Example 11.

Yield: 1.05 g (66% of theory).
Melting point: 255° C. (with decomposition).

EXAMPLE 19

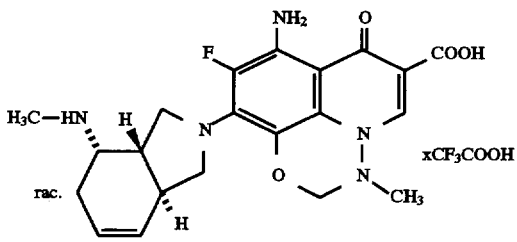

The tri fluoroacetic acid salt of 8-Amino-9-fluoro-3-methyl-10-((1SR,2SR,6SR)-2-methylamino-8-azabicyclo[4.3.0]non-4-en-8-yl)-7-oxo-2,3-dihydro-7H-pyrido-[1,2,3-d,e][1,2,3]benzoxadiazine-6-carboxylic acid The product of Example 18 (1.0 g; 1.9 mmol) is reacted with trifluoroacetic acid, as described in Example 15.

Yield: 1.0 g (97% of theory).
Melting point: 290° C. (with decomposition).

Preparation of the Intermediates

EXAMPLE A

8-Azabicyclo[4.3.0]non-2-ene
A.1. (E)-1-Bromo-2,4-pentadiene

Initially introduce 84 g (1.0 mol) of 1,4-pentadien-3-ol at 0° C. Add 150 ml (≈1.3 mol) of 48% strength aqueous hydrobromic acid dropwise with stirring such that the internal temperature does not exceed 5° C. After addition is complete, stir at room temperature for 1 h. The organic phase is separated off and reacted further without purification.

Yield: 107–129 g (73–88% of theory)
A.2. (E)-1-(2-Propenylamino)-2,4-pentadiene

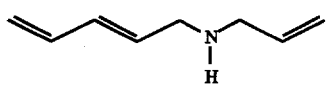

Initially introduce 228 g (4.0 mol) of 1-amino-2-propene. Add 58.8 g (0.4 mol) of (E)-1-bromo-2,4-pentadiene (title compound from Example A.1.) dropwise with stirring. Keep the internal temperature in the range from 20°–30° C. by cooling. Stir at room temperature for 5 h. Concentrate the mixture at 150 mbar. Add 20 g (0.5 mol) of sodium hydroxide dissolved in 200 ml of water, extract twice with 100 ml of methylene chloride each time, dry with sodium sulphate, add 0.1 g of 4-hydroxyanisole, concentrate and distil at 40 mbar. For stabilization, 10–20 ppm of 4-hydroxyanisole are added to the distillate.

Yield: 33–35 g (67–72% of theory)
Boiling point: 77°–82° C. at 40 mbar
$^1$H-NMR (CDCl$_3$): δ=6.07–6.48 (m, 2H); 5.64–6.07 (m, 2H); 5.00–5.27 (m, 4H); 3.19–3.36 ppm (m, 4H).

A.3. N-[(E)-2,4-Pentadienyl]-N-(2-propenyl)-acetamide

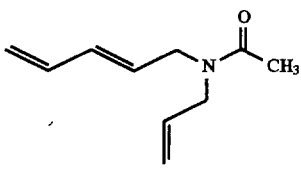

Initially introduce 24.6 g (0.2 mol) of (E)-1-(2-propenylamino)-2,4-pentadiene (title compound from Example A.2.), add 22.4 g of acetic anhydride dropwise and stir at room temperature overnight. Concentrate and react farther as a crude product.

A.4. 8-Acetyl-8-azabicyclo[4.3.0]non-2-ene

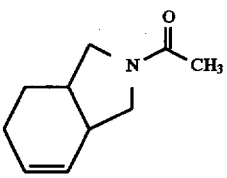

Dissolve 33.1 g (0.2 mol) of N-[(E)-2,4-pentadienyl]-N-(2-propenyl)-acetamide (title compound from Example A.3.) in 200 ml of xylene, introduce a vigorous stream of nitrogen for 15 min, add 0.1 g of 4-hydroxyanisole, then heat to reflux overnight and distil in a high vacuum.

Yield: 23.1 g (70% of theory based on the title compound from Example A.2.)
Boiling point: 88°–93° C. at 0.05 mbar
A.5. 8-Azabicyclo[4.3.0]non-2-ene

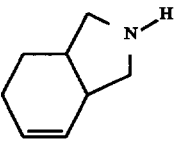

Heat 16.5 g (0.1 mol) of 8-acetyl-8-azabicyclo[4.3.0]non-2-ene (title compound from Example A.4.) to reflux for 3 h in a mixture of 100 ml of 45% strength sodium hydroxide solution, 50 ml of water and 100 ml of 1,2-ethanediol. After cooling, extract four times with 50 ml of diethyl ether each time. Dry combined organic phases with sodium sulphate and distil in a high vacuum.

Yield: 6.6 g (54% of theory)
Boiling point: 36°–44° C. at 0.35 mbar
$^1$H-NMR (CDCl$_3$): δ=5.79 (m, 1H); 5.74 (m, 1H); 3.02–3.17 (m, 2H); 2.47–2.72 (m, 2H); 2.06–2.30 (m, 2H); 1.91–2.06 (m, 2H); 1.68 (m, 1H); 1.45 ppm (m, 1H).

EXAMPLE B

Ethyl(1RS,2RS,6SR)-8-azabicyclo[4.3.0]non-4-ene-2-carboxylate (diastereomer A) and ethyl (1RS,2RS,6RS)-8-azabicyclo[4.3.0]non-4-ene-2-carboxylate (diastereomer B)

B.1. N-[(E)-2,4-Pentadienyl]-phthalimide

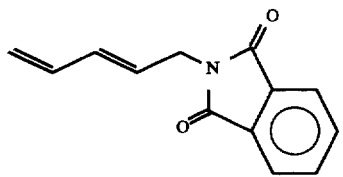

Initially introduce 185 g (1.0 mol) of potassium phthalimide in 800 ml of DMF. Add 147 g (1.0 mol) of (E)-1-bromo-2,4-pentadiene (title compound from Example A.1.) dropwise with stirring and at the same time keep the internal temperature below 30° C. by cooling. Stir at room temperature overnight. Then add the batch to 1.6 l of ice-water with stirring, filter off the precipitate, wash with water and dry at room temperature until constant weight is achieved.

Yield: 177–200 g (83–94% of theory)
Melting point: 118°–121° C. (sample recryst. from ethanol)
$^1$H-NMR (CDCl$_3$): δ=7.85 and 7.72 (m, 4H, aryl-H); 6.2–6.4 (m, 2H, H on C-3 and C-4); 5.75 (dt, 1H, H on C-2, J=14 and 6 Hz); 5.20 (d, 1H, H$_a$ on C-5, J=15 Hz); 5.10 (d, 1H, H$_b$ on C-5, J=8 Hz); 4.33 ppm (d, 2H, H on C-1, J=6 Hz).

B.2. (E)-1-Amino-2,4-pentadiene

400 g of bis-(2-aminoethyl)-amine and 213 g (1.0 mol) of N-[(E)-2,4-pentadienyl]-phthalimide (title compound from Example B.1.) are initially introduced into a 2 l distillation apparatus with a 10 cm Vigreux column and the mixture is heated to boiling at 60 mbar. The product distils in the range from 45°–60° C. at 60 mbar. For stabilization, 10–20 ppm of 4-hydroxyanisole are added to the distillate.

Yield: 71–80 g (86–96% of theory)
B.3. Ethyl (E)-4-[(E)-2,4-pentadienylamino]-2-butenoate

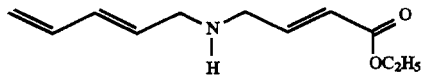

Initially introduce 41.6 g (0.5 mol) of (E)-1-amino-2,4-pentadiene (title compound from Example B.2.) and 50.6 g (0.5 mol) of triethylamine in 250 ml of THF at 0° C. and add dropwise 96.5 g (0.5 mol) of ethyl (E)-4-bromo-2-butenoate dissolved in 250 ml of THF. Keep the internal temperature below 5° C. by ice-cooling. Stir at 0° C. for 5 h and then at room temperature overnight. Add 500 ml of MTBE, then 500 ml of 1M sodium hydroxide solution, shake, phase separation, extract aqueous phase once with 100 ml of MTBE, dry combined organic phases with sodium sulphate, add 100 ml of toluene and 0.1 g of 4-hydroxyanisole and concentrate (avoid temperatures above 40° C. during he course of this). Purify residue by column chromatography on 1 kg of silica gel (63–200 µm) using cyclohexane/acetone 2:1. Before concentration again add 0.1 g of 4-hydroxyanisole and during concentration avoid temperatures above 40° C.

Yield: 52.7–58.6 g (54–60% of theory) of yellowish oil
Rf=0.24
$^1$H-NMR (CDCl$_3$): δ=6.99 (dt, 1H, J=15 and 5.5 Hz); 6.1–6.45 (m, 2H); 5.98 (d, 1H, J=15 Hz); 5.75 (dt, 1H, J=15 and 6.5 Hz), 5.18 (d, 1H, J=15 Hz); 5.06 (d, 1H, J=10 Hz); 4.19 (q, 2H); 3.42 (dd, 2H); 3.31 (d, 2H); 1.29 ppm (t, 3H).

B.4. Ethyl (1RS,2RS,6SR)-8-tert-butoxycarbonyl-8-azabicyclo[4.3.0]non-4-ene-2-carboxylate (diastereomer A) and ethyl (1RS,2RS,6RS)-8-tert-butoxycarbonyl-8-azabicyclo[4.3.0]non-4-ene-2-carboxylate (diastereomer B)

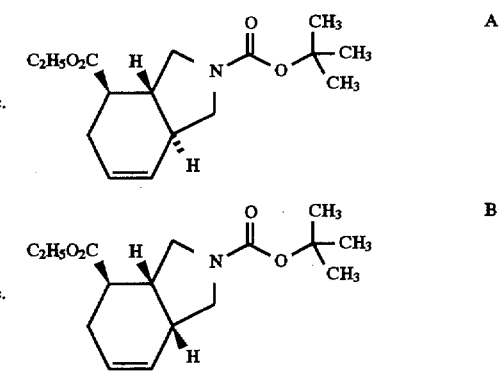

Initially introduce 97.5 g (0.5 mol) of ethyl (E)-4-[(E)-2,4-pentadienylamino]-2-butenoate (title compound from Example B.3.) dissolved in 250 ml of toluene. Add dropwise 114.5 g (0.525 mol) of di-tert-butyl dicarbonate dissolved in 250 ml of toluene and stir at room temperature overnight. Subsequently introduce a vigorous stream of nitrogen for 15 min, add 0.1 g of 4-hydroxyanisole, then heat to reflux for 6 h. Concentrate and purify residue by column chromatography on 1 kg of silica gel (63–200 µm) using cyclohexane/acetone 8:1.

Yield: 109–134 g (74–91% of theory) of yellowish oil; mixture of two diastereomers A and B in the ratio A:B=4:1
Rf=0.25
$^1$H-NMR (Cl$_2$DC-CDCl$_2$; 80° C.): δ=5.77 (m, 1H(A) and 1H(B)); 5.68 (m, 1H(A) and 1H(B)); 4.14 (m, 2H(A) and 2H(B)); 3.65 (m, 2H(A) and 1H(B)); 3.48 (dd, 1H(B)); 3.27 (dd, 1H(B)); 3.00 (m, 1H(A) and 1H(B)); 2.85 (dd, 1H(A)); 2.76 (m, 1H(B)); 2.60 (m, 1H(A)); 2.25–2.55 (m, 3H(A) and 4H(B)); 1.93 (m, 1H(A)); 1.51 (s, 9H(B)); 1.44 (s, 9H(A)); 1.25 ppm (t, 3H(A) and 3H(B)).

B.5. Ethyl (1RS,2RS,6SR)-8-azabicyclo[4.3.0]non-4-ene-2-carboxylate (diastereomer A) and ethyl (1RS,2RS,6RS)-8-azabicyclo[4.3.0]non-4-ene-2-carboxylate (diastereomer B)

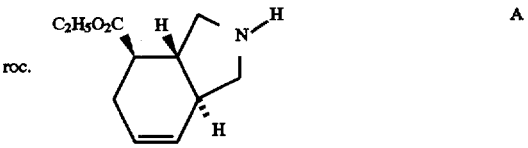

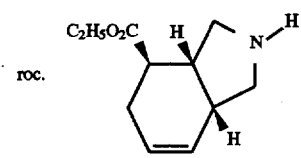

Initially introduce 6.0 g (20 mmol) of the title compound from Example B.4. in 20 ml of dioxane. Add 20 ml of conc. hydrochloric acid dropwise with cooling such that the internal temperature does not exceed 30° C. After addition is complete stir for 10 min. Add 40 ml of methylene chloride and add 40 ml of 20% strength ice-cooled sodium hydroxide solution dropwise with ice-cooling. Separate off organic phase, extract aqueous phase once with methylene chloride, dry combined organic phases with sodium sulphate and concentrate. Purify 3.0 g of crude product by column chromatography on 100 g of silica gel (63–200 μm) using cyclohexane/ethanol/17% strength aqueous ammonia (1:2:0.1).

Yield: 0.8 g of diastereomer A and 0.8 g of diastereomer B

Rf=0.79 title compound from Example B.4. 0.21 diastereomer B 0.11 diastereomer A $^1$H-NMR (CDCl$_3$): Diastereomer A: δ=5.83 (d, 1H); 5.69 (m, 1H); 4.15 (q, 2H); 3.21–3.38 (m, 2H); 2.52–2.89 (m, 3H); 2.21–2.52 (m, 3H); 1.95 (m, 1H); 1.28 ppm (t, 3H). Diastereomer B: δ=5.64–5.87 (m, 2H); 4.16 (q, 2H); 3.14–3.33 (m, 2H); 2.82 (dd, 1H); 2.15–2.74 (m, 6H); 1.28 ppm (t, 3H).

EXAMPLE C (1SR,2RS,6SR)-2-Ethoxycarbonylamino-8-azabicyclo[4.3.0]non-4-ene

C.1. (1RS,2RS,6SR)-8-tert-Butoxycarbonyl-8-azabicyclo-[4.3.0]non-4-ene-2-carboxylic acid

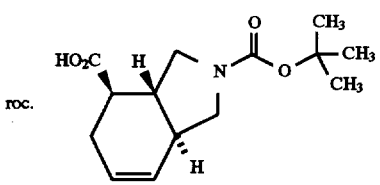

Initially introduce 30.8 g (0.55 mol) of potassium hydroxide dissolved in 500 ml of water. Add 147.7 g (0.5 mol) of the title compound from Example B.4. dissolved in 500 ml of methanol and stir at 60° C. under a nitrogen atmosphere for 8 h. After cooling, dilute reaction solution with 500 ml of water and slowly pour in 125 ml of acetic acid with stirring. After addition is complete allow to stand in the ice bath for 30 min, and filter off precipitate with suction, wash with water and dry at 50° C. to constant weight.

Yield: 84–98 g (63–73% of theory)

Melting point: 174°–176° C. (sample recrystallized from isopropanol/water 1:1)

$^1$H-NMR (Cl$_2$DC-CDCl$_2$; 80° C.): δ=5.83 (m, 1H, H on C-5); 5.74 (m, 1H, H on C-4); 3.65–3.80 (m, 2H, H$_a$ on C-7 and H$_a$ on C-9); 3.09 (dd, 1H, H$_b$ on C-9); 2.92 (dd, 1H, H$_b$ on C-7); 2.70 (m, 1H, H on C-2); 2.35–2.60 (m, 3H, H$_a$ and H$_b$ on C-3 and H on C-6); 2.01 (m, 1H, H on C-1); 1.5 ppm (s, 9H).

C.2. (1SR,2RS,6SR)-8-tert-Butoxycarbonyl-2-ethoxycarbonylamino-8-azabicyclo[4.3.0]non-4-ene

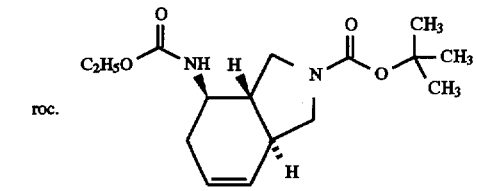

Initially introduce 53.3 g (0.2 mol) of the title compound from Example C.1. and 22.2 g (0.22 mol) of triethylamine dissolved in 200 ml of anhydrous THF. Add dropwise 22.8 g (0.21 mol) of ethyl chloroformate dissolved in 40 ml of THF while cooling with an ice/sodium chloride mixture such that the internal temperature does not exceed −10° C. After addition is complete, stir at low temperature for 1 h. Subsequently add an ice-cooled solution of 15.6 g (0.24 mol) of sodium azide in 50 ml of water dropwise with vigorous stirring such that the internal temperature does not exceed −10° C. After addition is complete, stir at low temperature for 30 min. Subsequently add 300 ml of water and 400 ml of toluene successively.

Separate off the organic phase, dry with sodium sulphate and concentrate at 15 mbar to half the original volume (bath temperature below 25° C.). Addition of 100 ml of ethanol, heat slowly with stirring (at the rate which evolution of nitrogen permits) and after evolution of nitrogen is complete reflux for 4 h. Concentrate and recrystallize crude product from methanol/water 85:15 and dry to constant weight at 50° C.

Yield: 24.2–28.5 g (39.46% of theory) of the title compound

Melting point: 120°–122° C.

$^1$H-NMR (CDCl$_3$): δ=5.78 and 5.73 (2d, 1H, H on C-5); 5.64 (m, 1H, H on C-4); (4.59 br. s, 1H, NH); 4.12 (m, 2H, ethoxy-CH$_2$); 3.90 (m, 1H, H on C-2); 3.74 and 3.67 (2m, 1H, H$_a$ on C-7); 3.67 and 3.56 (2m, 1H, H$_a$ on C-9); 3.12 (m, 1H, H$_b$ on C-9); 2.92 (m, 1H, H$_b$ on C-7); 2.67 (m, 1H, H$_a$ on C-3); 2.49 (m, 1H, H on C-6); 1.95 (m, 1H, H$_b$ on C-3); 1.83 (m, 1H, H on C-1); 1.46 (s, 9H); 1.24 ppm (m, 3H, ethoxy-CH$_3$).

Adjust the aqueous phase to a pH of 2–3 by addition of 10% strength hydrochloric acid, allow to stand in the ice bath for 30 min, filter off the precipitate with suction, wash with water and dry to constant weight at 50° C.

Yield: 16.0–19.2 g (30–36% of the title compound from Example C.1.) (recovered starting compound)

C.3. (1SR,2RS,6SR)-2-Ethoxycarbonylamino-8-azabicyclo[4.3.0]non-4-one

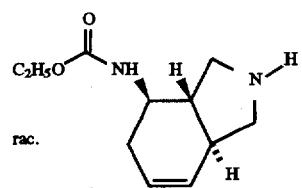

Initially introduce 31.0 g (0.1 mol) of the title compound from Example C.2. in 100 ml of a mixture of methanol/water (1:1) (suspension). Allow 100 ml of conc. hydrochloric acid to run in rapidly (slightly exothermic up to about 40° C., (a homogeneous solution is obtained) and stir until evolution of gas is complete (about 10 min). Add 200 ml of ice-water and add 70 ml of 45% strength sodium hydroxide solution dropwise with stirring and ice-cooling. Extract four times with 50 ml of methylene chloride each time, dry the combined organic phases with sodium sulphate, concentrate and strip off solvent residues in a high vacuum. The substance solidifies on concentration.

Yield: 13.7–16.6 g (65–79% of theory) of brownish pink-coloured, amorphous solid Rf=0.81 title compound from Example C.2. 0.11 title compound Methylene chloride/methanol/17% strength aqueous ammonia (15:4:0.5) ¹H-NMR (CDCl₃): δ=5.78 (d, 1H, H on C-5); 5.63 (m, 1H, H on C-4); 4.94 (br.d, 1H, NH); 4.10 (m, 2H, ethoxy-CH₂); 3.88 (m, 1H, H on C-2); 3.28 (m, 1H, $H_a$ on C-7); 3.19 (m, 1H, $H_a$ on C-9); 2.84 (m, 1H, $H_b$ on C-9); 2.57–2.62 (m, 2H, $H_a$ on C-3 and $H_b$ on C-7); 2.43 (m, 1H, H on C-6); 1.95 (m, 1H, $H_b$ on C-3); 1.79 (m, 1H, H on C-1); 1.23 ppm (m, 3H, ethoxy-CH₃).

EXAMPLE D (1SR,2RS,6SR)-2-Methylamino-8-azabicyclo[4.3.0]non-4-ene

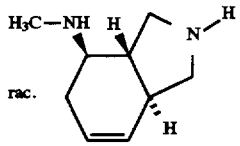

Initially introduce 1.9 g (50 mmol) of lithium aluminium hydride in 25 ml of anhydrous diethyl ether in a nitrogen atmosphere. Add dropwise 5.25 g (25 mmol) of the title compound from Example C.3. in 50 ml of anhydrous tetrahydrofuran and heat to reflux for 3 h. Add a further 0.95 g (25 mmol) of lithium aluminium hydride and again heat to reflux for 3 h. Slowly add water dropwise with ice-cooling until a white precipitate has formed. Filter off the precipitate with suction and boil twice with 100 ml of ethanol each time. Combine ethanol extracts with the mother liquor of the reaction, add 50 ml of toluene, concentrate and strip off solvent residues in a high vacuum.

Yield: 1.95 g (77% of theory) of amorphous solid

Rf=0.11

Methylene chloride/methanol/17% strength aqueous ammonia (2:4:1)

¹H-NMR (CDCl₃): δ=5.77 (d, 1H, H on C-5); 5.67 (m, 1H, H on C-4); 3.33 (dd, 1H, $H_a$ on C-7); 3.26 (dd, 1H, $H_a$ on C-9); 2.73–2.82 and 2.54–2.63 (2m, 4H, H on C-2, $H_a$ on C-3, $H_b$ on C-7 and $H_b$ on C-9); 2.41 (s, 3H, CH₃N); 2.34 (m, 1H, H on C-6); 1.90 (m, 1H, $H_b$ on C-3); 1.70 ppm (m, 1H, H on C-1).

EXAMPLE E (1RS,2RS,6SR)-2-Hydroxymethyl-8-azabicyclo[4.3.0]non-4-ene

E.1. (1RS,2RS,6SR)-8-tert-Butoxycarbonyl-2-hydroxymethyl-8-azabicyclo[4.3.0]non-4-ene (diastereomer A) and (1RS,2RS,6RS)-8-tert-butoxycarbonyl-2-hydroxymethyl-8-azabicyclo[4.3.0]non-4-ene (diastereomer B)

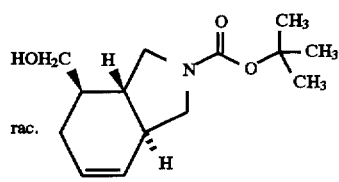

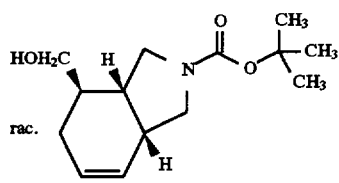

Initially introduce 29.5 g (0.1 mol) of the title compound from Example B.4. in 200 ml of anhydrous 1,2-dimethoxyethane in a nitrogen atmosphere. Add 150 ml of a 1.5M DIBAH solution in toluene (0.225 mol) dropwise at an internal temperature of <−65° C. After addition is complete remove cooling bath and allow to come to room temperature. Stir at room temperature for 2 h.

Add 60 ml of methanol dropwise with vigorous stirring (exothermic reaction); keep internal temperature between 35° and 45° C. by cooling with a cold water bath. Subsequently add 20 ml of 5% strength sodium hydroxide solution dropwise. After addition is complete stir for 10 min. Filter off precipitate with suction, boil twice with 150 ml of ethanol each time with stirring, combine ethanol extracts and reaction solution, concentrate, strip off solvent residues in a high vacuum and purify residue by column chromatography on 250 g of silica gel (63–200 μm) using cyclohexane/acetone (4:1).

Yield: 12.9–17.7 g (51–70% of theory) of yellowish oil; mixture of diastereomers A and B in the ratio 4:1

Rf=0.36 title compound from Example B.4. 0.12 title compound A and B

The crude product solidifies after relatively long standing. A diastereomerically pure sample of the main diastereomer A can be obtained from ether/petroleum ether by recrystallization.

¹H-NMR (CDCl₃): (diastereomer A) δ=5.67–5.82 (m, 2H, H on C-4 and C-5); 3.50–3.77 (m, 4H, $H_a$ on C-7, $H_a$ on C-9 and hydroxymethyl-CH₂); 3.02 (dt, 1H, $H_b$ on C-9); 2.85 (m, 1H, $H_b$ on C-7); 2.2–2.4 (m, 3H); 1.87–2.00 (m, 3H); 1.62 (m, 1H, H on C-1); 1.46 ppm (s, 9H).

E.2. (1RS,2RS,6SR)-2-Hydroxymethyl-8-azabicyclo[4.3.0]non-4-ene

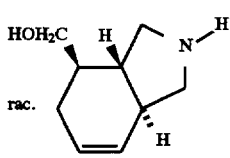

Initially introduce 2.5 g (10 mmol) of the title compound A from Example E.1. in 10 ml of methanol. Allow 10 ml of conc. hydrochloric acid to run in rapidly and stir for 30 min. Dilute to twice the volume with water then add 45% strength sodium hydroxide solution dropwise with stirring and ice-cooling up to a pH of ≧12. Concentrate, boil residue twice with ethanol with stirring, concentrate ethanol extracts and strip off solvent residues in a high vacuum.

Yield: 2.1 g (product contains NaCl residues)

Rf=0.20

Methylene chloride/methanol/17% strength aqueous ammonia (2:4:1)

$^1$H-NMR (d$_6$-DMSO): δ=5.76 (d, 1H); 5.62 (d, 1H); 3.47–3.56 (m, 2H, H$_a$ on C-7 and H$_a$ on C-9); 3.32–3.47 (m, 1H, H$_a$ from hydroxymethyl-CH$_2$); 3.23–3.32 (m, 1H, H$_b$ from hydroxymethyl-CH$_2$); 2.77 (t, 1H, H$_b$ on C-9); 2.64 (t, 1H, H$_b$ on C-7); 2.10–2.24 (m, 2H, H$_a$ on C-3 and H on C-6); 1.77–1.88 (m, 1H, H$_b$ on C-3); 1.69 (m, 1H, H on C-2); 1.40 ppm (m, 1H, H on C-1).

EXAMPLE F (1RS,2RS,6SR)-2-Ethoxycarbonylaminomethyl-8-azabicyclo[4.3.0]non-4-ene F.1. (1RS,2RS,6RS)-8-tert-Butoxycarbonyl-2-(4-toluenesulphonyloxymethyl)-8-azabicyclo[4.3.0]non-4-ene (diastereomer A) and (1RS,2RS,6RS)-8-tert-butoxycarbonyl-2-(4-toluenesulphonyloxymethyl-8-azabicyclo[4.3.0]non-4-ene (diastereomer B)

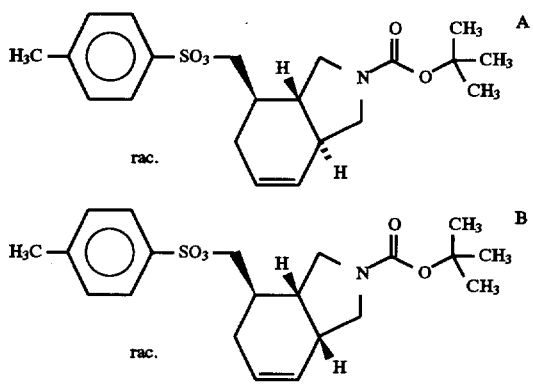

Initially introduce 12.7 g (0.05 mol) of the title compound from Example E.1. (crude mixture of diastereomers A and B) in 25 ml of anhydrous pyridine and cool to −15° C. Add 11.0 g (0.0575 mol) of 4-toluenesulphonyl chloride in portions such that the internal temperature does not exceed −5° C. After addition is complete stir at a temperature of −5° to −15° C. for 2 h, then at room temperature for 3 h. Add 5 g of ice, stir for 5 min, add to 50 ml of water, filter off precipitate with suction, wash with water and dry to constant weight at 50° C.

Yield: 14.4–16.3 g (71–80% of theory) pale pink-coloured solid

Mixture of diastereomers A and B

A diastereomerically pure sample of the main diastereomer A can be obtained by recrystallization from methanol.

Melting point: 111°–113° C.

$^1$H-NMR (CDCl$_3$): (diastereomer A) δ=7.79 (m, 2H, aryl-H); 7.36 (d, 2H, aryl-H); 5.74 and 5.78 (2d, 1H, H on C-5); 5.64 (m, 1H, H on C-4); 3.87–3.97 (m, 2H, tosyl-OCH$_2$-); 3.59 and 3.67 (2dd, 1H, H$_a$ on C-7); 3.48 (dd, 1H, H$_a$ on C-9); 2.78–2.96 (m, 2H, H$_b$ on C-7 and H$_b$ on C-9); 2.47 (s, 3H, aryl-CH$_3$); 2.22–2.36 (m, 2H, H$_a$ on C-3 and H on C-6); 2.06 (m, 1H, H on C-2); 1.80–1.98 (m, 1H, H$_b$ on C-3); 1.59 (m, 1H, H on C-1); 1.45 and 1.47 ppm (2s, 9H).

E.2. (1RS,2RS,6SR)-8-tert-Butoxycarbonyl-2-ethoxycarbonylaminomethyl-8-azabicyclo[4,3,0]non-4-ene (diastereomer A) and (1RS,2RS,6RS)-8-tert-butoxycarbonyl-2-ethoxycarbonylaminomethyl-8-azabicyclo[4.3.0]non-4ene (diastereomer B)

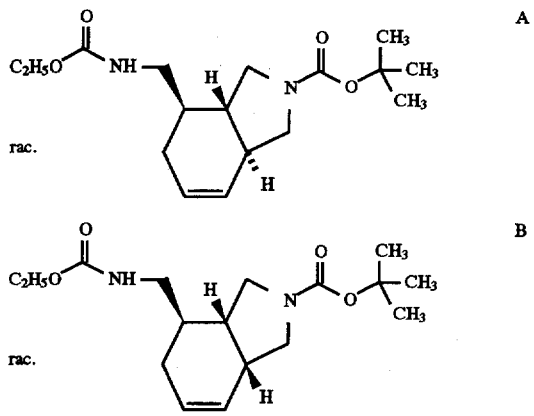

Heat 20.5 g (0.05 mol) of the title compound from Example F.1. (crude mixture of diastereomers A and B) and 6.5 g (0.1 mol) of sodium azide in 100 ml of DMF at 70° C. for 4 h. Add reaction solution to 200 ml of water, extract once with 200 ml of petroleum ether, wash the petroleum ether phase once with 50 ml of water, dry with sodium sulphate and concentrate at room temperature.

Take up the residue in 80 ml of THF and add dropwise to 13.1 g (0.05 mol) of triphenylphosphine dissolved in 80 ml of THF. After addition is complete stir at room temperature for 20 h, then slowly add 150 ml of water dropwise and after addition is complete stir for 15 min. Add hydrochloric acid dropwise with cooling (conc. HCl/water 1:3) until a pH of 3–4 is achieved, strip off THF in vacuo at room temperature, cool reaction solution to 0° C. and filter off precipitated triphenylphosphine oxide with suction (or take up with MTBE, if oily).

Adjust aqueous phase to a pH of ≧12 by addition of 10% strength sodium hydroxide solution, extract twice with 100 ml of methylene chloride each time, dry combined extracts with sodium sulphate, subsequently add 6.0 g (0.06 mol) of triethylamine, add 6.0 g (0.055 mol) of ethyl chloroformate dissolved in 20 ml of methylene chloride dropwise with stirring, stir at room temperature overnight, wash reaction solution once with 100 ml of water, dry withسsodium sulphate and concentrate.

Purify 23 g of crude product by column chromatography on 100 g of silica gel (63–200 μm) using cyclohexane/acetone (4:1).

Yield: 12.4 g (76% of theory) of viscous oil Mixture of diastereomers A and B

Rf values (cyclohexane/acetone 2:1): 0.32 diastereomer A 0.29 diastereomer B

The diastereomers A and B are separated by column chromatography on 250 g of silica gel (35–70 μm) using cyclohexane/acetone (8:1).

Yield: 4.3 g (26% of theory) of diastereomer A (viscous oil) 2.4 g (15% of theory) of mixed fraction 0.6 g (4% of theory) of diastereomer B $^1$H-NMR (Cl$_2$DC-CDCl$_2$; 80° C.): Diastereomer A: δ=5.75 (d, 1H, H on C-5); 5.66 (m, 1H, H on C-4); 4.67 (br, 1H, NH); 4.08 (q, 2H, ethoxy-CH$_2$); 3.62 (br, 2H, H$_a$ on C-7 and H$_a$ on C-9); 3.19 (br, 1H, H$_a$ on CH$_2$-NH); 3.05 (br, H$_b$ on CH$_2$-NH); 2.96 (dd, 1H, H$_b$ on C-9); 2.81 (dd, 1H, H$_b$ on C-7); 2.24–2.34 (m, 2H, H$_a$ on C-3 and H on C-6); 1.78–1.94 (m, 2H, H on C-2 and H$_b$ on C-3); 1.54 (m, 1H, H on C-1); 1.43 (s, 9H); 1.22 ppm (t, 3H, ethoxy-CH$_3$).

Diastereomer B: δ=5.69 (m, 1H, H on C-4); 5.57 (m, 1H, H on C-5); 4.65 (br, 1H, NH); 4.08 (q, 2H, ethoxy-CH$_2$); 3.52 (dd, 1H, H$_a$ on C-7); 3.41 (dd, 1H, H$_a$ on C-9); 3.29 (dd, 1H, H$_b$ on C-9); 3.24 (dd, 1H, H$_a$ on CH$_2$-NH); 3.03–3.12

(m, 2H, $H_b$ on C-7 and $H_b$ on $CH_2$-NH); 2.68 (m, 1H, H on C-6); 2.12–2.22 (m, 2H, H on C-1 and $H_a$ on C-3); 1.74–1.87 (m, 2H, H on C-2 and $H_b$ on C-3); 1.43 (s, 9H); 1.22 ppm (t, 3H, ethoxy-$CH_3$).

F.3. (1RS,2RS,6SR)-2-Ethoxycarbonylaminomethyl-8-azabicyclo[4.3.0]non-4-ene

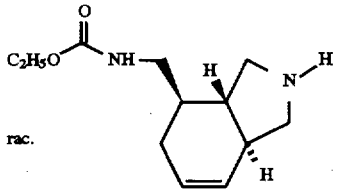

Initially introduce 1.6 g (5.7 mmol) of the title compound A from Example F.2. in 10 ml of methanol. Allow 8 ml of conc. hydrochloric acid to run in rapidly and stir for 30 min. Dilute to twice the volume with water then add 45% strength sodium hydroxide solution dropwise with stirring and ice-cooling up to a pH of $\geq 12$. Extract four times with methylene chloride, dry the combined organic phases with sodium sulphate, concentrate and strip off solvent residues in a high vacuum.

Yield: 0.8 g (63% of theory) of viscous oil
Rf=0.16
Methylene chloride/methanol/17% strength aqueous ammonia (15:4:0.5)

$^1$H-NMR ($CDCl_3$): $\delta$=5.81 (d, 1H, H on C-5); 5.67 (m, 1H, H on C-4); 5.00 (br, 1H, NH); 4.10 (q, 2H, ethoxy-$CH_2$); 3.18–3.28 and 3.08 (m, 3H and m, 1H: $H_a$ on C-7, $H_a$ on C-9, $H_a$ and $H_b$ on $CH_2$-NH-CO); 2.67 (dd, 1H, $H_b$ on C-9); 2.53 (dd, 1H, $H_b$ on C-7); 2.34 (m, 1H, $H_a$ on C-3); 2.25 (m, 1H, H on C-6); 1.79–1.96 (m, 2H, H on C-2 and $H_b$ on C-3); 1.50 (m, 1H, H on C-1); 1.24 ppm (t, 3H, ethoxy-$CH_3$).

EXAMPLE G (1RS,2SR,6RS)-2-Hydroxymethyl-8-azabicyclo[4.3.0]non-4-ene

G.1. (E)-1-tert-Butoxycarbonylamino-2,4-pentadiene

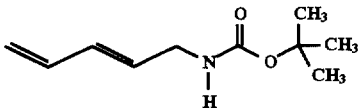

Initially introduce 8.3 g (0.1 mol) of (E)-1-amino-2,4-pentadiene (title compound from Example B.2.) in 50 ml of MTBE and add 20 mg of 4-hydroxyanisole. Subsequently add dropwise 22.9 g (0.105 mol) of di-tert-butyl dicarbonate dissolved in 50 ml of MTBE at an internal temperature of 20°–30° C. After addition is complete, stir at room temperature for 20 h. Concentrate and strip off residues of di-tert-butyl dicarbonate at 40° C. in a high vacuum.

Yield: 18.9 g (crude product) of colourless oil
Rf=0.25

Cyclohexane/acetone (4:1)

$^1$H-NMR ($CDCl_3$): $\delta$=6.05–6.43 (m, 2H, H on C-3 and C-4); 5.68 (dd, 1H, H on C-2, J=14 and 6 Hz); 5.17 (dd, 1H, $H_a$ on C-5, J=16 Hz); 5.07 (dd, 1H, $H_b$ on C-5, J=10 Hz); 4.75 (br, 1H, NH); 3.77 (t, 2H, H on C-1); 1.45 ppm (s, 9H).

G.2. (1RS,2RS,6RS)-2-tert-Butoxycarbonylaminomethyl-7,9-dioxo-8-oxabicyclo[4.3.0]non-3-ene

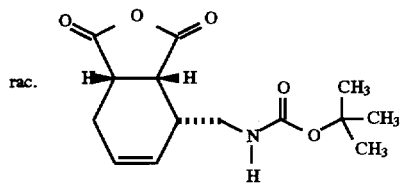

Initially introduce 83.2 g (1.0 mol) of (E)-1-amino-2,4-pentadiene (title compound from Example B.2.) in 250 ml of MTBE and add 0.1 g of 4-hydroxyanisole. Subsequently add dropwise 229.2 g (1.05 mol) of di-tert-butyl dicarbonate dissolved in 250 ml of MTBE at an internal temperature of 20°–30° C. After addition is complete stir at room temperature for 20 h. Concentrate reaction mixture and take up in 1 l of toluene. Add 103.0 g (1.05 mol) of maleic anhydride and stir at an internal temperature of 60° C. for 24 h. Filter off precipitate with suction, wash with toluene and dry to constant weight at 50° C.

Yield: 208.2 g (74% of theory) white, crystalline solid
Melting point: 157°–159° C.

$^1$H-NMR ($d_6$-DMSO): $\delta$=5.81 (m, 1H, H on C-4); 5.59 (d, 1H, H on C-3); 3.77 (dd, 1H $H_a$ on $CH_2$-NH); 3.44 (m, 2H, H on C-1 and $H_b$ on $CH_2$-NH); 2.94 (m, 1H, H on C-2); 2.66 (m, 1H, H on C-6); 2.16 (m, 1H, $H_a$ on C-5); 2.06 (m, 1H, $H_b$ on C-5); 1.43 ppm (s, 9H).

G.3. Methyl (1RS,2SR,6RS)-9-oxo-8-azabicyclo[4.3.0]non-4ene-2-carboxylate

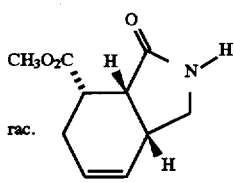

Initially introduce 83.2 g (1.0 mol) of (E)-1-amino-2,4-pentadiene (title compound from Example B.2.) in 250 ml of THF and add 0.1 g of 4-hydroxyanisole. Subsequently add dropwise 229.2 g (1.05 mol) of di-tert-butyl dicarbonate dissolved in 250 ml of THF at an internal temperature of 20°–30° C. After addition is complete stir at room temperature for 20 h. Add 103.0 g (1.05 mol) of maleic anhydride and heat to reflux for 5 h. Concentrate and take up the residue in 500 ml of methanol, add 30 ml of p-toluenesulphonic acid, then again heat to reflux for 5 h. After cooling, rapidly add dropwise a solution of 20 g of sodium carbonate dissolved in 500 ml of water with ice-cooling and stirring, allow mixture to stand for a further 30 min in the ice bath, filter off precipitate with suction, wash with a little water and dry to constant weight at 50° C.

Yield: 125–148 g (64–76% of theory) white, crystalline solid

Melting point: 190°–193° C.

$^1$H-NMR ($d_6$-DMSO): $\delta$=7.50 (s, 1H, NH); 5.77 (m, 1H, H on C-4); 5.56 (m, 1H, H on C-5); 3.60 (s, 3H, $CH_3O$); 3.42 (dd, 1H, $H_a$ on C-7); 3.16 (dd, 1H, H on C-1); 3.00 (m, 1H, H on C-6); 2.88 (dd, 1H, $H_b$ on C-7); 2.67 (m, 1H, H on C-2); 2.02–2.18 ppm (m, 2H, $H_a$ and $H_b$ on C-3).

G.4. (1RS,2SR,6RS)-2-Hydroxymethyl-8-azabicyclo[4.3.0]non-4-ene

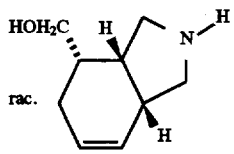

Initially introduce 19.6 g (0.1 mol) of the title compound from Example G.3. in 100 ml of THF under an inert gas atmosphere (suspension). Add dropwise 100 ml (0.15 mol) of 1.5M DIBAH solution in toluene at an internal temperature of 10°–20° C. Add dropwise the clear, homogeneous solution thus obtained to a suspension of 1.9 g of lithium aluminium hydride in 50 ml of THF. After addition is complete stir at room temperature for 15 min, then at reflux temperature for 30 min. After cooling, add 3.8 g (0.1 mol) of lithium aluminium hydride in portions, then heat to reflux for 24 h. After cooling successively add 50 ml of water and 10 ml of 1M sodium hydroxide solution dropwise, filter off the precipitate with suction and boil three times with 150 ml of ethanol each time. Combine filtrate and extracts and concentrate.

Yield: 16.4 g (product contains lithium hydroxide and aluminium hydroxide)

Rf=0.3

Methylene chloride/methanol/17% strength aqueous ammonia (2:4:1)

EXAMPLE H (1RS,2SR,6RS)-2-Ethoxycarbonylaminomethyl-8-azabicyclo[4.3.0]non-4-ene H.1. (1RS,2SR,6RS)-8-tert-Butoxycarbonyl-2-hydroxymethyl-8-azabicyclo[4.3.0]non-4-ene

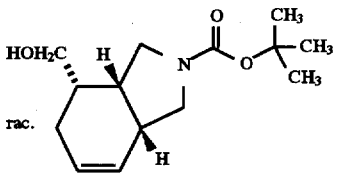

Dissolve 16.4 g of crude product from Example G.4. (corresponds to 0.1 mol of the title compound from Example G.4.) in 100 ml of THF. Add dropwise 22.9 g (0.105 mol) of di-tert-butyl dicarbonate dissolved in 100 ml of THF at an internal temperature of 0°–5° C., and stir at 0° C. for 24 h, then at room temperature for a further 24 h. Concentrate and purify crude product by column chromatography on 250 g of silica gel (63–200 μm) using cyclohexane/acetone (2:1).

Yield: 13.7 g (54% of theory over 2 stages); viscous oil

Rf=0.21 title compound 0.08 title compound from Example G.4.

H.2. (1RS,2SR,6RS)-8-tert-Butoxycarbonyl-2-(4-toluenesulphonyloxymethyl)-8-azabicyclo[4.3.0]non-4-ene

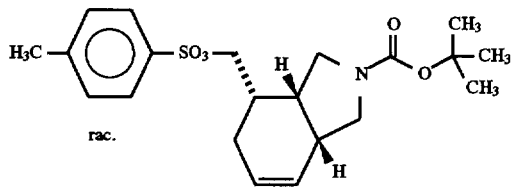

The title compound is obtained from the title compound of Example H.1. analogously to Example F.1.

Yield: 81–83% of theory

Melting point: 160°–162° C. $^1$H-NMR (CDCl$_3$): δ=7.79 (m, 2H, aryl-H); 7.37 (d, 2H, aryl-H); 5.67 (m, 1H, H on C-4); 5.47 (m, 1H, H on C-5); 3.78–3.97 (m, 2H, tosyl-OCH$_2$-); 3.13–3.42 (m, 3H, CH$_2$-N); 2.95 (t, 1H, CH$_2$-N); 2.74 (m, 1H); 2.54 (m, 1H); 2.47 (s, 3H, aryl-CH$_3$); 2.32 (m, 1H, H on C-2); 2.06 (m, 1H, H$_a$ on C-3); 1.66–1.83 (m, 1H, H$_b$ on C-3); 1.44 ppm (s, 9H).

H.3. (1RS,2SR,6RS)-8-tert-Butoxycarbonyl-2-ethoxycarbonylaminomethyl-8-azabicyclo[4.3.0]non-4-ene

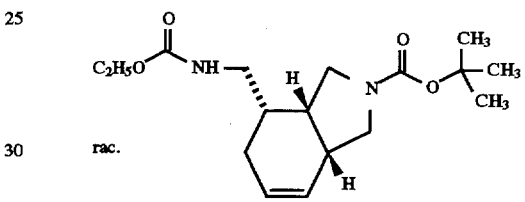

The title compound is obtained from the title compound of Example H.2. analogously to Example F.2.

Purify crude product by column chromatography on silica gel (63–200 μm) using cyclohexane/acetone (2:1).

Yield: 76% of theory; clear, viscous oil

Rf=0.35 (cyclohexane/acetone 2:1)

$^1$H-NMR (Cl$_2$DC-CDCl$_2$; 80° C.): δ=5.69 (m, 1H, H on C-4); 5.47 (d, 1H, H on C-5); 4.59 (br, 1H, NH); 4.10 (q, 2H, ethoxy-CH$_2$); 3.38 (dd, 1H); 3.32 (m, 1H); 3.24 (m, 1H); 3.01–3.08 (m, 3H); 2.79 (m, 1H); 2.47 (m, 1H); 2.07 (m, 2H); 1.78 (m, 1H); 1.42 (s, 9H); 1.22 ppm (t, 3H, ethoxy-CH$_3$).

H.4. (1RS,2SR,6RS)-2-Ethoxycarbonylaminomethyl-8-azabicyclo[4.3.0]non-4-ene

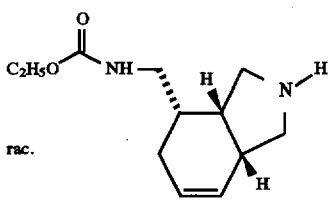

The title compound is obtained from the title compound of Example H.3. analogously to Example C.3.

Yield: 42% of theory

Rf=0.93 title compound from Example H.3. 0.23 title compound

Methylene chloride/methanol/17% strength aqueous ammonia (15:4:0.5)

EXAMPLE I (1SR,2RS,3RS,6SR)-2-Ethoxycarbonylamino-3-methyl-8-azabicyclo[4.3.0]non-4-ene I.1. N-[(2E,4E)-2,4-Hexadienyl]-phthalimide

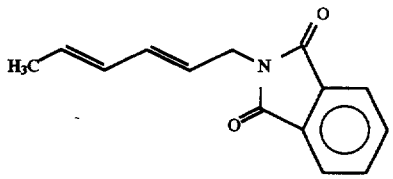

The title compound is obtained from (2E,4E)-1-bromo-2,4,-hexadiene analogously to Example B.1.

Yield: 77–79% of theory

Melting point: 114°–117° C. (sample recryst. from ethanol)

$^1$H-NMR (CDCl$_3$): δ=7.85 (m, 2H); 7.72 (m, 2H); 6.25 (dd, 1H); 6.00 (ddd, 1H); 5.5–5.8 (m, 2H); 4.29 (d, 2H); 1.74 ppm (d, 3H).

I.2. (2E,4E)-1-Amino-2,4-hexadiene

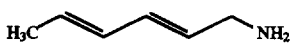

The title compound is obtained from the title compound of Example I.1. analogously to Example B.2.; boiling range: 40°–70° C. at 16–18 mbar.

Yield: 67–83% of theory

I.3. Ethyl (E)-4-[(2E,4E)-2,4-hexadienylamino]-2-butenoate

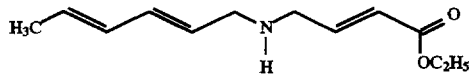

The title compound is obtained from the title compound of Example I.2. analogously to Example B.3.

Yield: 46% of theory $^1$H-NMR (CDCl$_3$): δ=6.98 (dt, 1H); 5.9–6.25 (m, 3H); 5.5–5.8 (m, 2H); 4.19 (q, 2H); 3.40 (dd, 2H); 3.27 (d, 2H); 1.76 (d, 3H); 1.29 ppm (t, 3H).

I.4. Ethyl (1RS,2RS,3RS,6SR)-8-tert-Butoxycarbonyl-3-methyl-8-azabicyclo[4.3.0]non-4-ene-2-carboxylate (Diastereomer A) and ethyl (1RS,2RS,3SR, 6RS)-8-tert-Butoxycarbonyl-3-methyl-8-azabicyclo[4.3.0]non-4-ene-2-carboxylate (Diastereomer B)

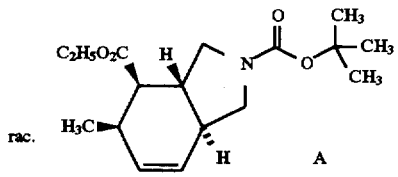

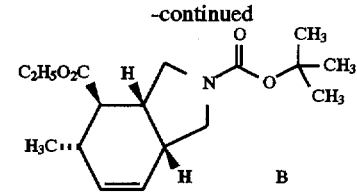

The title compounds are obtained from the title compound of Example I.3. analogously to Example B.4.

Yield: 70% of theory; mixture of 2 diastereomers A and B in the ratio A:B=4:1.

Rf=0.49 (cyclohexane/acetone 2:1)

I.5. (1RS,2RS,3RS,6SR)-8-tert-Butoxycarbonyl-3-methyl-8-azabicyclo[4.3.0]non-4-ene-2-carboxylic acid

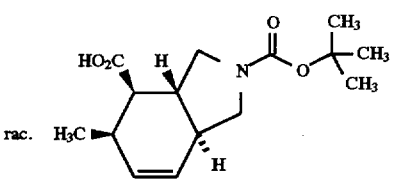

Initially introduce 1.17 g (21 mmol) of potassium hydroxide dissolved in 20 ml of water. Add 5.9 g (19 mmol) of the title compound from Example I.4. dissolved in 20 ml of methanol and heat at reflux under a nitrogen atmosphere for 48 h. Concentrate, take up in water, extract once with methylene chloride, adjust the aqueous phase to pH 3–4 with acetic acid, filter off precipitate with suction, wash with water, dry at room temperature and recrystallize from cyclohexane/acetone 6:1.

Yield: 2.25 g (42% of theory)

Melting point: 189° C.

$^1$H-NMR (d$_6$-DMSO): δ=5.77 (d, 1H); 5.61 (m, 1H); 3.67 (m, 1H); 3.54 (m, 1H); 2.61–2.95 (m, 4H); 2.30 (m, 1H); 1.82 (m, 1H); 1.40 (s, 9H); 0.90 ppm (d, 3H).

I.6. (1SR,2RS,3RS,6SR)-8-tert-Butoxycarbonyl-2-ethoxycarbonylamino-3-methyl-8-azabicyclo[4.3.0]non-4-ene

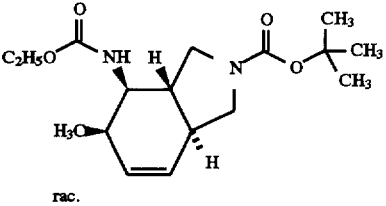

The title compound is obtained from 2.25 g (8 mmol) of the title compound of Example I.5. analogously to Example C.2. Changed compared with Example C.2.: reflux in ethanol for 8 h instead of 4 h; purification by column chromatography on 100 g of silica gel (63–200 μm) using toluene/ethyl acetate (2:1).

Yield: 1.6 g (59% of theory) of clear oil $^1$H-NMR (CDCl$_3$): δ=5.68 and 5.72 (2d, 1H); 5.61 (m, 1H); 4.81 (m 1H); 4.0–4.2 (m, 3H); 3.53 (m), 3.62 (m) and 3.72 (dd) [2H]; 3.08 (t, 1H); 2.92 (t, 1H); 2.75 (m, 1H); 2.47 (m, 1H); 1.83 (m, 1H); 1.47 (m, 9H); 1.25 (m, 3H); 0.97 ppm (d, 3H).

I.7. (1SR,2RS,3RS,6SR)-2-Ethoxycarbonylamino-3-methyl-8-azabicyclo[4.3.0]non-4-ene

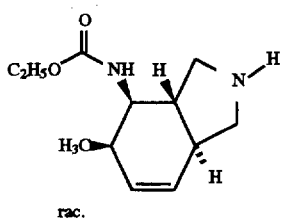
rac.

The title compound is obtained from 1.6 g (4.7 mmol) of the title compound from Example I.6. analogously to Example C.3.

Yield: 0.7 g (70% of theory) of yellowish oil; Rf=0.09

Methylene chloride/methanol/17% strength aqueous ammonia (15:4:0.5)

EXAMPLE K (1RS,2RS,6RS)-2-Ethoxycarbonylaminomethyl-8-azabicyclo[4.3.0]non-4-ene K.1. Diethyl 3-phthalimidomethyl-cyclohex-4-ene-1,2-dicarboxylate

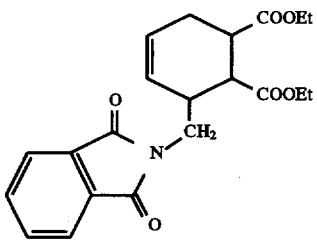

10.67 g (50 mmol) of N-[(E)-2,4-pentadienyl]-phthalimide (title compound from Example B.1.) and 8.61 g of diethyl fumarate are heated at reflux for 2 days in 50 ml of toluene. The mixture is concentrated and the residue is chromatographed on silica gel (eluent: cyclohexane/acetone 8:1).

Yield: 14.8 g (77% of theory)

Melting point: 80°–84° C.

K.2. Ethyl (1RS,2RS,6RS)-9-oxo-8-azabicyclo[4.3.0]non-4-ene-2-carboxylate (A) and ethyl(1RS,2RS,6SR)-9-oxo-8-azabicyclo[4.3.0]non-4-ene-2-carboxylate (B)

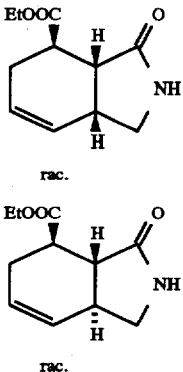

150.3 g (0.39 mol) of the title compound from Example K.1. are initially introduced in 720 ml of ethanol and 173.3 g (2.9 mol) of ethylenediamine are added dropwise with ice-cooling. The mixture is stirred at room temperature for 20 h, concentrated in vacuo, diluted with water (about 700 ml), adjusted to pH 2–3 with conc. hydrochloric acid and extracted three times with 500 ml of dichloromethane in each case. The organic phase is dried (sodium sulphate) and concentrated in vacuo. The diastereomers are separated by chromatography (eluent: cyclohexane/acetone 1:1).

Yield: 36.7 g of product A (45% of theory)

Rf=0.47 (cyclohexane/acetone 1:1)

27.0 g of product B (45% of theory)

RF=0.22 (cyclohexane/acetone 1:1)

K3. (1RS,2RS,6RS)-2-Hydroxymethyl-8-azabicyclo[4.3.0]non-4-ene

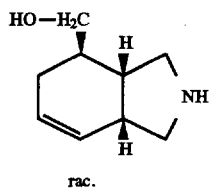
rac.

5.2 g (25 mmol) of ethyl (1RS,2RS,6RS)-9-oxo-8-azabicyclo[4.3.0]non-4-ene-2-carboxylate (product A from Example K.2.) are dissolved in 50 ml of tetrahydrofuran under a nitrogen atmosphere and 130 ml of a 1.5 molar di(isobutyl)aluminium hydride solution (195 mmol) are subsequently added dropwise. The solution is heated under reflux for 16 h. After reaction is complete, 60 ml of methanol, 30 ml of tert-butyl methyl ether and 10 ml of water are added dropwise successively and solids are filtered off with suction with the addition of Tonsil. The suction filter residue is stirred twice with a mixture of ethanol/conc. ammonia/water (10:1:1) and filtered off with suction again. The purified filtrate are concentrated and the crude product is purified by chromatography (eluent: dichloromethane/methanol/conc. ammonia 2:4:1).

Yield: 2.7 g (71% of theory)

$^1$H-NMR (DMSO-$d_6$): 5.69 (m, 1H, 4-H); 5.60 (m, 1H, 5-H); 3.39 (dd, 1H, 10a-H); 3.26 (dd, 1H, 10b-H); 2.97 (m, 2H, 7a-H, 9a-H), 2.63 (m, 1H, 9b-H); 2.38 (bs, 1H, 6-H)M; 2.32 (dd, 1H, 7b-H); 2.06 (m, 1H, 3a-H); 1.95 (m, 1H, 1-H); 1.77 (m, 1H, 3b-H); 1.44 ppm (m, 1H, 2-H).

K.4. (1RS,2RS,6RS)-8-tert-Butoxycarbonyl-2-hydroxymethyl-8-azabicyclo[4.3.0]non-4-ene

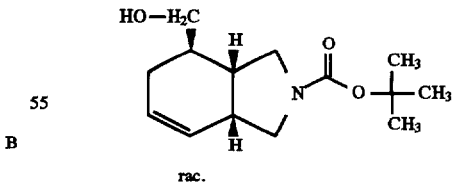
rac.

The product from Example K.3. (8.87 g; 58 mmol) is reacted as described in Example H.1.

Yield: 11.0 g (75% of theory)

RF=0.25 (cyclohexane/acetone 2:1)

K.5. (1RS,2RS,6RS)-8-tert-Butoxycarbonyl-2-(4-toluenesulphonyloxymethyl)-8-azabicyclo[4.3.0]non-4-ene

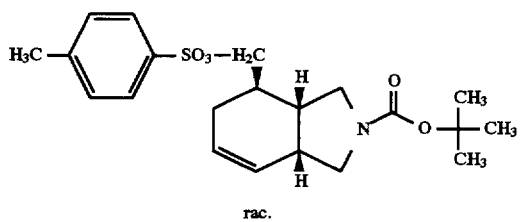

The title compound is obtained from the product of Example K.4. in analogy to Example F.1.

Yield: 97% of theory

RF=0.40 (cyclohexane/acetone 2:1)

K6. (1RS,2RS,6RS)-8-tert-Butoxycarbonyl-2-azidomethyl-8-azabicyclo[4.3.0]non-4-ene

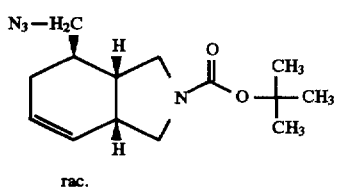

A solution of 33 g (0.08 mol) of (1RS,2RS,6RS)-8-tert-butoxycarbonyl-2-(4-toluenesulphonyloxymethyl)-8-azabicyclo[4.3.0]non-4-ene (title compound from Example K.5.) and 15.8 g (0.24 mol) of sodium azide in 200 ml of N,N-dimethylformamide is stirred at 70° C. for 40 h. The cooled solution is diluted with water (500 ml) and extracted three times with 250 ml of petroleum ether each time. The combined organic phase is washed with 5% strength sodium hydrogen carbonate solution, dried (sodium sulphate) and concentrated.

Yield: 21.6 g (97%)

$^1$H-NMR (CDCl$_3$): 5.71 (m, 1H, C=CH); 5.58 (m, 1H, C=CH); 3.61-3.22 (m 2H); 3.10 (m, 1H); 2.70 (bs, 1H); 2.24 (m, 2H); 1.91 (m, 2H), 1.47 ppm (s, 9H, tert-butyl).

K.7. (1RS,2RS,6RS)-8-tert-Butoxycarbonyl-2-aminomethyl-8-azabicyclo[4.3.0]non-4-ene

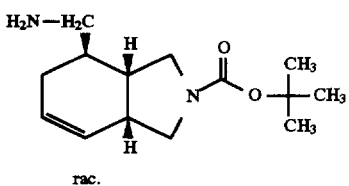

A solution of the azido compound from Example K.6. (21.6 g; 78 mmol) in 150 ml of pyridine/water (5:1) is saturated with hydrogen sulphide with ice-cooling and subsequently left at room temperature for 20 h. After conversion is complete, it is concentrated in vacuo and redistilled several times with toluene, and the residue is chromatographed (eluent: cyclohexane/acetone 1:1).

Yield: 11.0 g (66% of theory)

RF=0.12 (cyclohexane/acetone 1:1)

K.8. (1RS,2RS,6RS)-8-tert-Butoxycarbonyl-2-(ethoxycarbonylaminomethyl-8-azabicyclo[4.3.0]non-4-ene

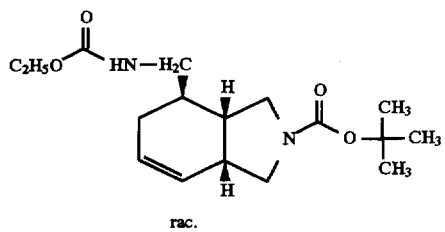

3.7 g (15 mmol) of (1RS,2RS,6RS)-8-tert-butoxycarbonyl-2-aminomethyl-8-azabicyclo[4.3.0]non-4-ene are initially introduced in 40 ml of dioxane and 15 ml of water, 2.3 g (16 mmol) of potassium carbonate are added and 1.75 g (16 mmol) of ethyl chloroformate are added dropwise at room temperature. After stirring for two hours, the mixture is concentrated in vacuo, the residue is taken up in dichloromethane (70 ml), and the solution is extracted twice by shaking with 25 ml of water each time, dried (sodium sulphate) and concentrated. The crude product is purified by chromatography (cyclohexane/acetone 2:1).

Yield: 2.8 g (59% of theory)

RF=0.53 (cyclohexane/acetone 1:1).

K9. (1RS,2RS,6RS)-2-(Ethoxycarbonylaminomethyl)-8-azabicyclo[4.3.0]non-4-ene

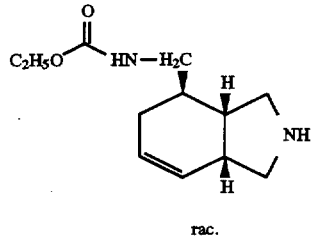

7.6 g (23 mmol) of the product from Example K.8. are initially introduced in 100 ml of methanol/water (1:1) and 30 ml of half-concentrated hydrochloric acid are allowed to run in at room temperature. After the evolution of gas is complete, the mixture is stirred for 30 minutes, diluted with ice-water (about 100 ml) and adjusted to pH 12 with conc. sodium hydroxide solution. The aqueous phase is extracted four times with 100 ml of dichloromethane each time. The extracts are combined, dried over sodium sulphate and concentrated in vacuo.

Yield: 3.9 g (76% of theory)

RF=0.45 (dichloromethane/methanol/conc. ammonia (2:4:0.1)

EXAMPLE L (1RS,2RS,6RS)-2-Aminomethyl-8-azabicyclo[4.3.0] non-4-ene-bistrifluoromethanesulphonate

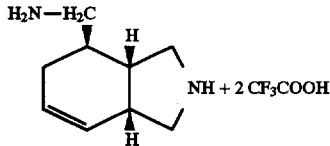

A solution of 2.0 g (8 mmol) of (1RS,2RS,6RS)-8-tert-butoxycarbonyl-2-aminomethyl-8-azabicyclo[4.3.0]non-4- ene (product from Example K.7.) in 30 ml of dichloromethane is treated with 30 ml of trifluoroacetic acid and left at room temperature for 30 minutes. The solvent and the acid are distilled off in the presence of toluene and the mixture is redistilled several times with toluene. The product is dried over potassium hydroxide/phosphorus pentoxide (1:1) in a vacuum desiccator.

Yield: 1.5 g of brown oil $^1$H-NMR (DMSO-d$_6$): 5.78 (m, 1H, C=CH); 5.60 (m, 1H, C=CH); 3.34 (M, 2H); 3.03 (m, 1H), 2.87 (m, 2H), 2.73 (m, 1H); 2.45 (m, 1H); 2.34 (m, 1H); 2.22 (M, 1H); 1.94 ppm (m, 2H).

FAB-MS: M+1=153.

EXAMPLE M (1RS,2RS,6RS)-2-Ethoxycarbonylaminomethyl-8-azabicyclo[4.3.0]non-4-ene (This product is identical to the title compound from Example F.)

M.1. (1RS,2RS,6SR)-2-Hydroxymethyl-8-azabicyclo[4.3.0]non-4-ene

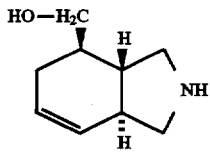

rac.

Ethyl (1RS,2RS,6RS)-9-oxo-8-azabicyclo[4.3.0]non-4-ene-2-carboxylate (product B from Example K.2.) is reacted analogously to Example K.3.

Yield: 75% of theory

RF=0.22 (dichloromethane/methanol/conc. ammonia (15:4:0.5)

M.2. (1RS,2RS,6SR)-8-tert-Butoxycarbonyl-2-hydroxymethyl-8-azabicyclo[4.3.0]non-4-ene

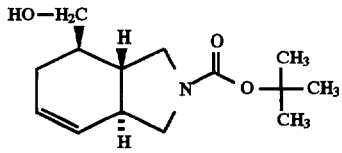

rac.

The product from Example M.1. is reacted analogously to Example K.4.

Yield: 64% of theory

RF=0.23 (cyclohexane/acetone 2:1)

M.3. (1RS,2RS,6SR)-8-tert-Butoxycarbonyl-2-(4-toluenesulphonyloxymethyl)-8-azabicyclo[4.3.0]non-4-ene

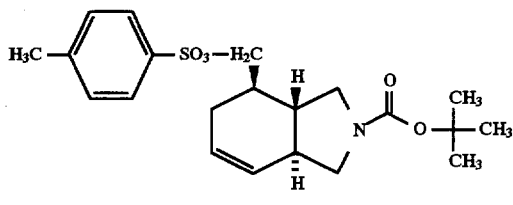

rac.

The title compound is obtained from the product of Example M.2. in analogy to Example F.1.
Yield: 91–98% of theory
RF=0.59 (cyclohexane/acetone 2:1)

M.4. (1RS,2RS,6SR)-8-tert-Butoxycarbonyl-2-azidomethyl-8-azabicyclo[4.3.0]non-4-ene

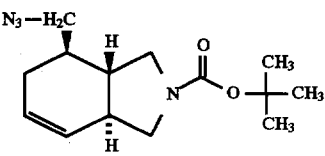

rac.

A solution of 13.0 g (32 mmol) of the product from Example M.3. in 80 ml of N,N-dimethylformamide is treated with 4.15 g (64 mmol) of sodium azide and stirred at 70° C. for 4 h. The same amount of sodium azide is then added again and the mixture is stirred at 100° C. for a further 6 h. It is then worked up as described in Example K.6.
Yield: 7.0 g (79% of theory)
RF=0.55 (cyclohexane/acetone 2:1)

M.5. (1RS,2RS,6SR)-8-tert-Butoxycarbonyl-2-aminomethyl-8-azabicyclo[4.3.0]non-4-ene

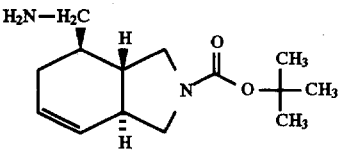

rac.

The azido compound from Example M.4. is reacted as described in Example K.7.

Chromatography is carried out using methanol/dichloromethane/conc. ammonia (15:2:0.1).
Yield: 75% of theory
RF=0.12 (methanol/dichloromethane/conc. ammonia 15:2:0.1)

M.6. (1RS,2RS,6SR)-8-tert-Butoxycarbonyl-2-(ethoxycarbonylmethyl)-8-azabicyclo[4.3.0]non-4-ene

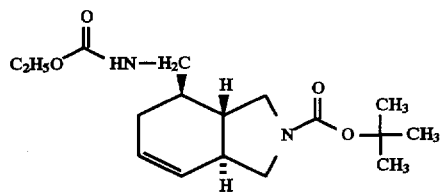

rac.

4.3 g (17 mmol) of the amino compound from Example M.5. and 1.9 g (19 mmol) of triethylamine are initially introduced in 50 ml of dichloromethane, 2.2 g (20 mmol) of ethyl chloroformate dissolved in 10 ml of dichloromethane are added dropwise at 0° C. and the mixture is stirred at room temperature for 24 h. The solution is treated with water (50 ml) and the phases are separated. The aqueous phase is extracted a further three times with 40 ml of dichloromethane each time. The organic phases are combined, dried (sodium sulphate) and concentrated.

Yield: 5.3 g (96% of theory)

¹H-NMR (CDCl₂-CDCl₂, 80° C.): 5.79 (ddd, 1H, C=CH); 5.58 (m 1H, C=CH); 4.61 (bs, 1H, carbamate-NH); 4.23 (m, 1H); 4.12 (q, 2H, ethyl-CH₂); 3.99 (m, 1H); 3.20-3.08 (m, 2H); 2.82 (m, 2H); 2.25 (m, 2H); 2.09 (m, 1H); 1.84 (m, 2H); 1.42 (s, 9H, tert-butyl); 1.37 ppm (t, 3H, ethyl-CH₃).

M.7. (1RS,2RS,6SR)-2-(Ethoxycarbonylaminomethyl)-8-azabicyclo[4.3.0]non-4-ene (1RS,2RS,6SR)-8-tert-Butoxycarbonyl-2-(ethoxycarbonylaminomethyl)-8-azabicyclo[4.3.0]non-4-ene is reacted as described in Example K.9.

Yield: quantitative

RF=0.55 (methanol/dichloromethane/conc. ammonia 15:4:0.5)

EXAMPLE N (1SR,2RS,6RS)-2-Methylamino-8-azabicyclo[4.3.0]non-ene

N.1. (1RS,2RS,6RS)-9-Oxo-azabicyclo[4.3.0]non-4-ene-2-carboxylic acid

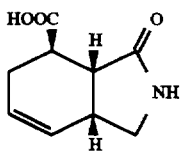

8.36 g (40 mmol) of ethyl (1RS,2RS,6RS)-9-oxo-8-azabicyclo[4.3.0]non-4ene-2-carboxylate (product A from Example K.2.) are stirred at 60° C. for 40 h with 30 ml of water and 5 ml of conc. sulphuric acid. The product precipitates on cooling. The precipitate is washed with a little cold water and dried at 50° C. in a vacuum drying oven.

Yield: 4.80 g (66% of theory)

¹H-NMR (DMSO-d₆): 12.35 (s, 1H, COOH); 7.60 (s, 1H, lactam-NH); 5.74 (m, 1H, C=CH); 5.59 (m, 1H, C=CH); 3.45 (dd, 1H, 7a-H); 2.95-2.85 (m, 4H, 1-H, 2-H, 6-H, 7b-H); 2.29 (m, 1H, 3a-H); 2.00 ppm (m, 1H, 3b-H).

N.2. (1SR,2RS,6RS)-2-Ethoxycarbonylamino-9-oxo-8-azabicyclo[4.3.0]non-4-ene

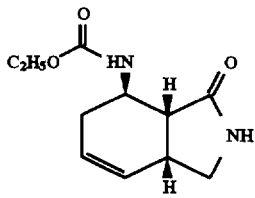

(1RS,2RS,6RS)-9-Oxo-8-azabicyclo[4.3.0]non-4-ene-2-carboxylic acid (title compound from Example N.1.) is reacted analogously to Example C.2.

Yield: 68% of theory

RF=0.06 (cyclohexane/acetone 1:1)

N3. (1SR,2RS,6RS)-2-Methylamino-8-azabicyclo[4.3.0]non-4-ene

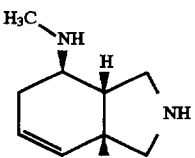

The title compound is obtained by reacting the product from Example N.2. with 10 equivalents of di(isobutyl) aluminium hydride analogously to Example K.3. and working up.

Yield: 51% of theory

¹H-NMR (CDCl₃): 5.72 (m, 1H, C=CH); 5.68 (m, 1H, C=CH); 3.19-3.10 (m, 2H); 2.88 (dd, 1H); 2.60 (dd, 1H); 2.50 (m, 1H); 2.44 (s, 3H, N-CH₃); 2.33-2.28 (m, 2H); 2.19 (m, 1H); 1.89 ppm (m, 1H).

EXAMPLE O (1SR,2SR,6RS)-2-Methylamino-8-azabicyclo[4.3.0]non-4-ene

O.1. (1RS,2SR,6RS)-9-Oxo-8-azabicyclo[4.3.0]non-4-ene-2-carboxylic acid

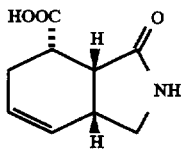

0.2 g of conc. sulphuric acid, 25 ml of water and 25 ml of acetic acid are initially introduced at 60° C. 9.8 g (50 mmol) of the product from Example G.3. are added in small portions. The mixture is stirred at 60° C. for 5 h. For working up, a solution of 0.8 g of sodium hydrogen carbonate in 10 ml of water is added and the mixture is concentrated in vacuo. The residue is suspended in 40 ml of water and brought into solution by addition of conc. sodium hydroxide solution with ice-cooling. After insoluble components have been filtered off with suction, the mixture is rendered acidic with half-concentrated hydrochloric acid and again cooled to 0° C. The product which precipitates is washed with a little cold water and is subsequently dried at 50° C. in a vacuum drying oven.

Yield: 4.8 g (53% of theory)

Melting point: 192°–193° C.

O.2. (1SR,2SR,6RS)-2-Ethoxycarbonylamino-9-oxo-8-azabicyclo[4.3.0]non-4-ene

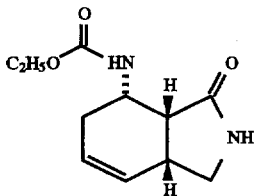

rac.

(1RS,2SR,6RS)-9-Oxo-8-azabicyclo[4.3.0]non-4-ene-2-carboxylic acid (title compound from Example O.1.) is reacted as described in Example C.2.

Yield: 68% of theory
Melting point: 160°–164° C.

O.3. (1SR,2SR,6RS)-2-Methylamino-8-azabicyclo[4.3.0]non-4-ene

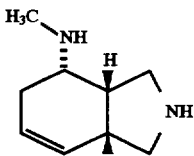

rac.

The title compound is obtained by reacting the product from Example O.2. with 10 equivalents of di(isobutyl)aluminium hydride analogously to Example K.3. and working up.

Yield: 81% of theory $^1$H-NMR (CDCl$_3$): 5.72 (m, 1H, C=CH); 5.50 (m, 1H, C=CH); 3.04-2.77 (m, 6H); 2.60 (m; 1H); 2.49 (s, 3H, N-CH$_3$); 2.31 (bs, 2H, 2×NH); 2.25 (m, 1H); 1.89 ppm (m, 1H).

EXAMPLE P 9,10-Difluoro-3-methyl-8-nitro-7-oxo-2,3-dihydro-7H-pyrido[1,2,3-d,e][1,3,4]-benzoxadiazine-6-carboxylic acid 3.7 g (36.6 mmol) of potassium nitrate are added in portions to 7.0 g (24.8 mmol) of 9,10-difluoro-3-methyl-7-oxo-2,3-dihydro-7H-pyrido[1,2,3-d,e][1,3,4]-benzoxadiazine-6-carboxylic acid dissolved in 90 ml of concentrated sulphuric acid and stirred at room temperature for one hour. The reaction mixture is added to 270 ml of ice-water. The resulting precipitate is filtered off with suction, washed with water and dried.

Yield: 6.9 g (85% of theory)
Melting point: >300° C.

EXAMPLE Q

8-Amino-9,10-difluoro-3-methyl-7-oxo-2,3-dihydro-7H-pyrido[1,2,3-d,e][1,3,4]-benzoxadiazine-6-carboxylic acid 4.0 g (12.2 mmol) of 9,10-difluoro-3-methyl-8-nitro-7-oxo-2,3-dihydro-7H-pyrido[1,2,3-d,e][1,3,4] benzoxadiazine-6-carboxylic acid and 1.2 g of palladium on active carbon (10% palladium) are suspended in 280 ml of ethanol and hydrogenated at room temperature under normal pressure for two days. The reaction mixture is treated with 280 ml of water and then adjusted to pH 10–11 with 2N sodium hydroxide solution. The hydrogenation catalyst is filtered off and the filtrate is adjusted to pH 5–6 with 2N hydrochloric acid. The resulting precipitate is filtered off, washed with methanol and dried (fraction A). The hydrogenation catalyst filtered off is heated under reflux for one hour three times in 100 ml of dimethylformamide (DMF) each time and then filtered again. The combined DMF solutions are concentrated in vacuo and dried (fraction B).

Yield: 3.0 g (83% of theory)
Melting point: >300° C.

We claim:

1. An 8-amino-10(azabicycloalkyl)-pyrido[1,2,3-d,e][1,3,4]benzoxadiazine of the formula

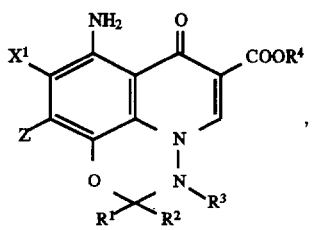

(I)

in which

R$^1$ represents hydrogen or C$_1$–C$_4$-alkyl which is optionally substituted by hydroxyl or halogen, R$^2$ independently of R$^1$ represents hydrogen or methyl, R$^3$ represents hydrogen or C$_1$–C$_4$-alkyl, R$^4$ represents hydrogen, alkyl having 1 to 4 carbon atoms, which is optionally substituted by hydroxyl, methoxy, amino, methylamino or dimethylamino, or (5-methyl-2-oxo-1,3-dioxol-4-yl)-methyl, X$^1$ represents hydrogen or halogen, Z represents a radical of the structure

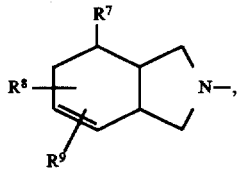

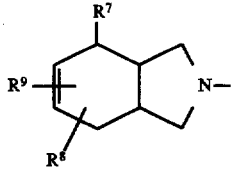

or

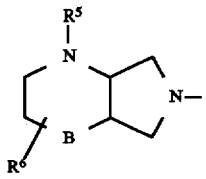

in which

R$^7$ represents hydrogen, hydroxyl, —NR$^{10}$R$^{11}$, hydroxymethyl, —CH$_2$—NR$^{10}$R$^{11}$, carboxyl, methoxycarbonyl or ethoxycarbonyl, where R$^{10}$ represents hydrogen, C$_1$–C$_3$-alkyl which is optionally substituted by hydroxyl, represents alkoxycarbonyl having 1 to 4 atoms in the alkoxy moiety or represents $C_1$-$C_3$-acyl and, $R^{11}$ represents hydrogen or methyl, $R^8$ represents hydrogen, straight-chain or branched $C_1$-$C_3$-alkyl or cyclopropyl, $R^9$ represents hydrogen or methyl, $R^6$ represents hydrogen or methyl, $R^5$ represents hydrogen, methyl or radicals with the structures —CH=CH—$CO_2R^{5'}$, —$CH_2$—$CH_2$—$CO_2R^{5'}$, —$CH_2$—CO—$CH_3$, or —$CH_2$—$CH_2$—CN, $R^{5'}$ represents methyl or ethyl, and B represents —$CH_2$—, O or a direct bond, or a pharmaceutically utilizable hydrate, acid addition, alkali metal, alkaline earth metal, silver or guanidinium salt thereof.

2. An 8-amino-10(azabicycloalkyl)-pyrido [1,2,3-d,e][1,3,4]benzoxadiazine, hydrate or salt thereof according to claim 1, in which $R^1$ represents hydrogen or $C_1$-$C_3$alkyl which is optionally substituted by hydroxyl, $R^2$ independently of $R^1$ represents hydrogen or methyl, $R^3$ represents hydrogen, methyl or ethyl, $R^4$ represents hydrogen, alkyl having 1 to 4 carbon atoms, which is optionally substituted by hydroxyl, methoxy, amino, methylamino or dimethylamino, or (5-methyl-2-oxo-1,3-dioxol-4-yl)-methyl, $X^1$ represents hydrogen, fluorine or chlorine, Z represents a radical of the structure

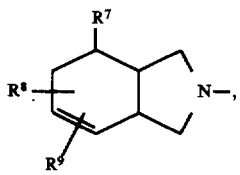

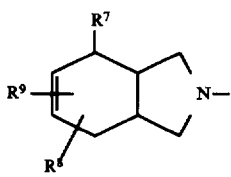

or

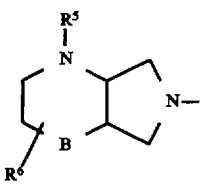

in which $R^7$ represents hydrogen, hydroxyl, —$NR^{10}R^{11}$, hydroxymethyl or —$CH_2$—$NR^{10}R^{11}$, where $R^{10}$ represents hydrogen, $C_1$-$C_2$-alkyl which is optionally substituted by hydroxyl, represents alkoxycarbonyl having 1 to 4 C atoms in the alkoxy moiety or represents $C_1$-$C_3$-acyl and, $R^{11}$ represents hydrogen or methyl, $R^8$ represents hydrogen, straight-chain or branched $C_1$-$C_3$-alkyl or cyclopropyl, $R^9$ represents hydrogen or methyl, $R^5$ represents hydrogen or methyl, $R^6$ represents hydrogen, and B represents —$CH_2$—, O or a direct bond.

3. An 8-amino-10(azabicycloalkyl)-pyrido[1,2,3-d,e][1,3,4]benzoxadiazine according to claim 1, in which $R^1$ represents hydrogen or methyl, $R^2$ represents hydrogen, $R^3$ represents methyl or ethyl, $R^4$ represents hydrogen, methyl or ethyl, $X^1$ represents fluorine, Z represents a radical of the structure

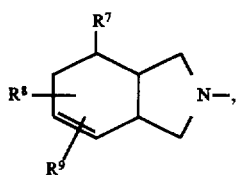

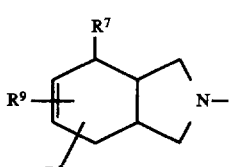

or

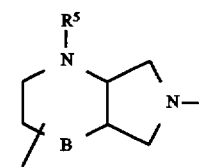

in which $R^7$ represents hydrogen, hydroxyl, —$NR^{10}R^{11}$, hydroxymethyl or —$CH_2$—$NR^{10}R^{11}$, $R^{10}$ represents hydrogen, methyl, alkoxycarbonyl having 1 to 4 C atoms in the alkoxy moiety or $C_1$-$C_3$-acyl, $R^{11}$ represents hydrogen or methyl, $R^8$ represents hydrogen, straight-chain or branched $C_1$-$C_3$-alkyl or cyclopropyl, $R^6$ represents hydrogen, $R^9$ represents hydrogen or methyl, $R^5$ represents hydrogen or methyl, and B represents —$CH_2$—, O or a direct bond.

4. An antibacterial composition comprising an antibacterially effective amount of a compound, hydrate or salt thereof according to claim 1, and a pharmaceutically acceptable diluent.

5. A method of combating bacteria which comprises applying to such bacteria or a locus from which is desired to exclude such bacteria an antibacterially effective amount of a compound, hydrate or salt thereof according to claim 1.

6. A compound of the formula

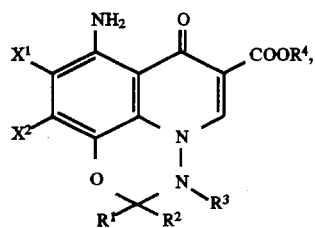

(II)

in which

R¹ represents hydrogen or $C_1$–$C_4$-alkyl which is optionally substituted by hydroxyl or halogen,
R² independently of R¹ represents hydrogen or methyl,
R³ represents hydrogen or $C_1$–$C_4$-alkyl,
R⁴ represents hydrogen, alkyl having 1 to 4 carbon atoms, which is optionally substituted by hydroxyl, methoxy, amino, methylamino or dimethylamino, or (5-methyl-2-oxo-1,3-dioxo-4-yl)-methyl,
X¹ represents hydrogen or halogen, and
X² represents halogen.

* * * * *

UNITED STATES PATENT AND TRADEMARK OFFICE
CERTIFICATE OF CORRECTION

PATENT NO.   : 5,679,675
DATED        : October 21, 1997
INVENTOR(S)  : Jaetsch, et al.

It is certified that error appears in the above-indentified patent and that said Letters Patent is hereby corrected as shown below:

Col. 68, line 46    After " -CH -NR$^{10}$R$^{11}$, " insert -- where --

Signed and Sealed this

Seventeenth Day of November, 1998

Attest:

BRUCE LEHMAN

Attesting Officer    Commissioner of Patents and Trademarks